(12) United States Patent
Heldman et al.

(10) Patent No.: US 8,843,201 B1
(45) Date of Patent: *Sep. 23, 2014

(54) WEARABLE, UNSUPERVISED TRANSCRANIAL DIRECT CURRENT STIMULATION (TDCS) DEVICE FOR MOVEMENT DISORDER THERAPY, AND METHOD OF USING

(71) Applicants: Dustin A Heldman, Shaker Heights, OH (US); Joseph P Giuffrida, Hinckley, OH (US)

(72) Inventors: Dustin A Heldman, Shaker Heights, OH (US); Joseph P Giuffrida, Hinckley, OH (US)

(73) Assignee: Great Lakes NeuroTechnologies Inc., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/045,336

(22) Filed: Oct. 3, 2013

Related U.S. Application Data

(63) Continuation of application No. 13/633,358, filed on Oct. 2, 2012, now Pat. No. 8,583,238.

(51) Int. Cl.
*A61N 1/00* (2006.01)
*A61N 1/20* (2006.01)

(52) U.S. Cl.
CPC ...................................... *A61N 1/20* (2013.01)

USPC .......................................................... 607/45

(58) Field of Classification Search
USPC .......................................................... 607/45
See application file for complete search history.

(56) References Cited

U.S. PATENT DOCUMENTS 7,805,196 B2 * 9/2010 Miesel et al. .................. 607/45

\* cited by examiner

*Primary Examiner* — George Manuel
(74) *Attorney, Agent, or Firm* — Brian Kolkowski

(57) ABSTRACT

The present invention relates to a system and methods for noninvasively providing therapy for movement disorder symptoms. The present invention provides such a therapy system which provides trans-cranial direct current stimulation (tDCS) in order to treat those symptoms and the disorders. The present invention further provides such tDCS therapy while the subject sleeps in order to minimize the time required and impact of the therapy on the subject's waking life. The system, methods, and devices of the present invention are intended to provide a low-dose electrical current, trans-cranially, to a specific area of the subject's brain while he or she sleeps in order to decrease the occurrence, severity, and duration of the symptoms of movement disorders. The present invention aims to reduce the amount of medication necessary, counteract the effects of medication wearing off during sleep, and to overall improve the quality of life of subjects suffering from movement disorders.

20 Claims, 10 Drawing Sheets

WEARABLE, UNSUPERVISED TRANSCRANIAL DIRECT CURRENT STIMULATION (TDCS) DEVICE FOR MOVEMENT DISORDER THERAPY, AND METHOD OF USING

CROSS-REFERENCE TO RELATED APPLICATIONS

This application is a continuation of co-pending U.S. patent application having Ser. No. 13/633,358 filed on Oct. 2, 2012.

STATEMENT REGARDING FEDERALLY-SPONSORED RESEARCH OR DEVELOPMENT

The U.S. Government has a paid-up license in this invention and the right in limited circumstances to require the patent owner to license others on reasonable terms provided for by the terms of the Phase I grant number 1R43NS077652-01A1 awarded by the National Institute of Neurological Disorders and Stroke.

BACKGROUND OF THE INVENTION

1. Field of the Invention

The present invention relates to therapeutic medical apparatus, systems, devices and/or methods, and more particularly, to apparatus and methods for using neural stimulation to alleviate the symptoms of movement disorders, such as those associated with Parkinson's disease, essential tremor, dystonia, and Tourette's syndrome, including tremor, bradykinesia, rigidity, gait/balance disturbances, and dyskinesia, as well as sleep disorders such as REM sleep behavior disorder and restless leg syndrome.

2. Technical Background

There has been tremendous growth and active research into disease modifying agents of Parkinson's disease (PD) as well as pharmaceutical and surgical treatments for associated motor symptoms. PD, a neurodegenerative disorder that affects the motor system, is characterized by tremor, slowed movements (bradykinesia), and rigidity. With approximately 1.5 million Americans diagnosed with PD and over 50,000 new cases each year, the need for intervention to both treat the symptoms and alter disease progression cannot be understated. Overnight transcranial direct current stimulation (tDCS), which provides a noninvasive painless electrical polarization to the cerebral cortex, could provide a non-pharmaceutical and non-surgical therapeutic option to complement current treatments for PD motor symptoms and related sleep disturbances.

PD is caused by a loss of dopamine-producing neurons in the substantia nigra, but the exact reason for neurodegeneration remains unknown. A current trend in the treatment of diseases identified as being associated with the central nervous system is the stimulation of target areas of the central nervous system to effect therapeutic benefit. Such stimulation has been accomplished with, for example, implanted electrodes that deliver electrical stimulation to target brain regions; one class of electrical neural stimulation devices has been categorized under the name "deep brain stimulation" (DBS). Although the exact neurological mechanisms by which DBS therapies succeed are complex and are not yet fully understood, such therapies have proven effective in treating Parkinson's disease motor symptoms (such as tremor, bradykinesia, rigidity, and gait disturbances), and investigation into the use of DBS for the treatment of this and other neurological and mental health disorders, including major depression, obsessive-compulsive disorder, tinnitus, obesity, criminal tendencies, and antisocial disorders, is ongoing.

Typically, medication for Parkinson's disease (PD) consists of Levodopa to alleviate symptoms. Over time, however, the medication has reduced efficacy and shows increased occurrence of side effects such as dyskinesias. Once side effects outweigh benefits, subjects consider deep brain stimulation (DBS). An electrode/wire lead is implanted in a specific location in the brain which shows hyperactivity in PD subjects and is sensitive to electrical stimulation. PD target sites are the subthalamic nucleus (STN) or globus pallidus internus (GPi). The essential tremor and Parkinson tremor target site is generally the ventral intermedius nucleus of the thalamus (VIM). Electrical pulses characterized by amplitude (volts), current (amps), frequency (Hz), and pulse width (microseconds) are regulated by an implantable pulse generator (IPG) placed beneath the skin on the chest. Stimulation affects motor symptoms on the contralateral side, i.e., right side tremor will be treated on the left brain. After a subject has been implanted and recovered, programming sessions will fine tune stimulation settings described above in order to minimize symptom severity, minimize side effects, and maximize IPG battery life span. Although medication is not eliminated, it is typically reduced significantly. DBS efficacy decreases over time as the body adjusts to stimulation and protein buildup around electrode lead attenuates electrical field. Programming sessions are required throughout the subject's lifetime, though the frequency of adjustments are typically greater at first.

A typical implanted DBS stimulation lead consists of a thin insulated needle comprising four platinum/iridium electrodes spaced 0.5 or 1.5 mm apart along the length of the lead. One or multiple leads may be implanted in a target brain region or regions to provide symptom-inhibiting high-frequency stimulation, although some research suggests that excellent results can be achieved even when the lead is implanted distant from a target region. A DBS lead is connected to an implantable pulse generator (IPG), which serves as a controller and power source, via an extension cable tunneled subcutaneously to a subcutaneous pocket in the chest or abdominal cavity. The IPG typically includes a battery and circuitry for telemetered communication with an external programming device used to adjust, or "tune," DBS lead stimulation parameters, which may include stimulation frequency, amplitude, pulse width (or wavelength), and contact configuration (that is, the selection of which electrodes are utilized from among the four electrodes available on a lead, and, if two or more electrodes are active, the relative polarity of each). These parameters are initially set during implantation surgery and are then further fined-tuned in the outsubject clinic or in a doctor's office following surgery to maximize therapeutic benefit and minimize undesirable stimulation-induced side effects. The first such tuning session usually takes place several weeks following implantation surgery, after the subject has recovered and inflammation at the lead placement site has subsided.

While existing drug and DBS treatments do alleviate motor symptoms, new data has documented that tDCS has therapeutic potential in PD both acutely and chronically. tDCS is a noninvasive brain simulation modality in which direct current is steadily applied via electrodes on the surface of the scalp. tDCS polarizes the brain using weak direct currents that are applied via scalp electrodes. Finite element models (FEM) show that current densities in the cortex resulting from tDCS are 2-3 orders of magnitude lower than action potential thresholds, thus, tDCS does not stimulate cortex, but rather modulates cortical excitability. Fregni et al. found that Unified Parkinson's Disease Rating Scale (UPDRS) scores improved significantly after anodal stimulation to primary motor cortex (M1) ($p<0.001$), F. Fregni et al., *Noninvasive cortical stimulation with transcranial direct current stimulation in Parkinson's disease*, Mov. Disord. 2006 October; 21(10):1693-1702. The current standard in evaluating the severity of movement disorder symptoms in Parkinson's disease is the Unified Parkinson's Disease Rating Scale (UPDRS) used to score motor tests, many of which involve repetitive movement tasks such as touching the nose and drawing the hand away repeatedly, or rapidly tapping the fingers together. A battery of exercises, typically a subset of the upper extremity motor section of the UPDRS, is normally completed during DBS lead placement surgery and subsequent programming sessions to evaluate performance while a clinician qualitatively assesses symptoms. Each test is evaluated by a clinician based solely on visual observation and graded on a scale that ranges from 0 (normal) to 4 (severe). More recently, Benninger et al. found that tDCS did not significantly improve overall UPDRS scores; however, bradykinesia, the primary complaint in many PD subjects, did significantly decrease ($p<0.0001$). D. H. Benninger et al., *Transcranial direct current stimulation for the treatment of Parkinson's disease*, Journal of Neurology, Neurosurgery & Psychiatry. 2010 September; 81(10):1105-1111. The fact that Chen states that tDCS as a treatment for PD is "not ready for prime time," but does emphasize that pilot studies are needed and "useful adjunctive treatments are clearly welcome," serves to point out that tDCS for movement disorder therapy is far from known in the art, but has shown potential for utility in this field. R. Chen, *Transcranial direct current stimulation as a treatment for Parkinson's disease—interesting, but not ready for prime time*, Journal of Neurology, Neurosurgery & Psychiatry. 2010 June; 81(10): 1061-1061. In addition to likely improving motor function in PD subjects, tDCS has been established and shown to have efficacy in various other fields, such as to aid in rehabilitation after stroke, improve motor learning in healthy adults, improve memory in subjects with Alzheimer's disease, improve mood in subjects with major depression, and improve memory during slow-wave sleep. Recent studies have shown that DBS during sleep either directly or as a function of increased mobility improves sleep quality in PD subjects, suggesting the tDCS may too improve sleep quality. A. W. Amara et al., *The effects of deep brain stimulation on sleep in Parkinson's disease*, Ther. Adv Neurol. Disord. 2011 January; 4(1):15-24.

Unlike other noninvasive stimulation modalities such as transcranial electrical stimulation (TES) and rapid transcranial magnetic stimulation (rTMS) that can be costly, painful, and cause side effects including seizures and psychotic symptoms, tDCS is painless, poses few side effects, and is ideal for home use since it can be provided in an inexpensive and compact package. The only sensation from tDCS is tingling during stimulation onset. This in sharp contrast to rTMS, which induces a strong scalp sensation along with facial and scalp muscle twitches. Additionally, rTMS systems are extremely bulky, require a large power supply, cost $20,000-$100,000, and are not suitable for home use. Conversely, the disclosed tDCS system will be specifically designed for home use and be much more cost effective.

In light of the above, it is therefore an object of the present invention to provide a noninvasive movement disorder therapy system, and methods of using the same, which can reduce the severity and frequency of a subject's symptom occurrence, improve the subject's sleep quality, and improve the subject's overall quality of life while reducing the amount of the subject's waking life required to receive such therapy.

SUMMARY OF THE INVENTION

The present invention relates to a system and methods for noninvasively providing therapy for movement disorder symptoms. The present invention provides such a therapy system which provides transcranial direct current stimulation (tDCS) in order to treat those symptoms and the disorders. The present invention further provides such tDCS therapy while the subject sleeps in order to minimize the time required and impact of the therapy on the subject's waking life. The system, methods, and devices of the present invention are intended to provide a low-dose electrical current, trans-cranially, to a specific area of the subject's brain while he or she sleeps in order to decrease the occurrence, severity, and duration of the symptoms of movement and/or sleep disorders. The present invention aims to reduce the amount of medication necessary, counteract the effects of medication wearing off during sleep, and to overall improve the quality of life of subjects suffering from movement disorders.

Preferably, the system or monitor is constructed to be rugged, so as to withstand transport, handling and to reliably survive daily use by the subject. The system or monitor should preferably be splash-proof (or water tight), dust-tight, scratch-resistant, and resistant to mechanical shock and vibration. The system or monitor should preferably be portable so the subject may travel with the device as necessary.

The system or monitor should preferably be capable of non-expert use. By this, it is meant that a person should not be required to possess extraordinary or extensive special medical training in order to use the system effectively and reliably. The system should therefore preferably be user-friendly in operation in a number of respects. First, the system should be capable of easy donning and doffing, substantially error-proof alignment and placement of the device on the subject's head. Second, the system should preferably have automatic detection of input signal quality; for example, the system should be capable of detecting an imbalance in electrode impedances, physiological and environmental artifacts, and electrical interferences and noise. Third, the system should preferably be capable of automatically detecting the subject's state or level of consciousness. Fourth, the system should preferably be capable of automatically providing a therapeutic direct current to the subject's brain without the need for user interaction.

Preferably, the system should operate in real time. One example of real-time operation is the ability of the system to detect the subject's level of consciousness and implement a current control protocol accordingly. Another example of real-time operation is the ability of the system to detect an improper or faulty connection, position, or signal of an electrode and cease providing a direct electrical current to that electrode or all electrodes. The system described in this invention also preferably incorporates a number of unique features that improve safety, performance, durability, and reliability. The system should be limited in the level or strength of the current that may be supplied to the subject. The placement of the electrodes should be readily ascertainable, repeatable, and not easily moved once in place. Integrated impedance sensors will automatically stop stimulation if the device is removed from the head.

All embodiments of the present invention include a wearable device to be placed on the subject's head while he or she sleeps. In some embodiments, the wearable device will be custom fitted to each subject to ensure proper electrode placement. In other embodiments, the wearable device will comprise a small patch-like apparatus which can be placed on the subject's head before sleep and discarded upon awaking.

As the subject sleeps, painless tDCS will be provided at specified intervals. In order to provide the necessary current, all embodiments of the present invention will include a current generation device. The current generation device should be capable of providing a direct current over a period of time with little or no variation in the current.

Many embodiments of the brain function monitor comprise an electrode lead or electrode array. At least one electrode may be utilized, and in such embodiment, the electrode is a typical tDCS electrode known to those in the art. More preferably, at least two electrodes may be utilized: at least one for injection of the direct current, and at least one for return of the direct current. Even more preferably, at least 5 electrodes are used. In the five electrode array, at least one electrode is used to deliver the current, and at least 4 electrodes are present for return of the current from the subjects brain. Other electrode arrangements, configurations, and placements are also contemplated for use with the system.

The system will not be designed to replace PD medication but rather will augment therapy and may result in a reduction of required medication use. Since subjects often feel worst in the morning after medication from the previous day has worn off, stimulation during the night may help subjects wake up feeling better. Additionally, designing the device for overnight use will make the system convenient and accessible so subjects need not worry about using the device in public or during their daily activities. Development will focus on treating the motor symptoms of PD; however, the proposed system may prove beneficial for overall sleep quality or other PD-related sleep disorders.

One embodiment of the present invention includes a method of providing therapy for movement disorder symptoms comprising steps of providing a wearable apparatus comprising at least two surface scalp electrodes, at least one electrode for providing a low dose direct electrical current to the patient, and at least one electrode for return of the low dose direct electrical current, placing the apparatus on a subject's head and having the subject wear the apparatus during sleep, and providing a low dose direct electrical current from the at least one surface scalp electrode for providing a low dose direct electrical current across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms, wherein cortex modulation in frontal regions, contralateral motor regions, and occipital lobe of the subject's brain is minimized to be less than 0.01 V/m.

Another embodiment of the present invention includes method of providing therapy for movement disorder symptoms comprising steps of providing a wearable apparatus, providing an array of at least five surface scalp electrodes, at least one central anodal electrode surrounded by at least four return electrodes arranged in a ring around the anodal electrode, affixing or embedding the electrode array to the wearable apparatus, placing the apparatus on a subject's head and having the subject wear the apparatus during sleep, and providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms, wherein the low dose electrical current is provided at 2 milli-amps (mA).

Yet another embodiment of the present invention includes a method of providing therapy for movement disorder symptoms comprising steps of providing a wearable apparatus, providing an array of at least five surface scalp electrodes, at least one central anodal electrode surrounded by at least four return electrodes arranged in a ring around the anodal electrode, affixing or embedding the electrode array to the wearable apparatus, placing the apparatus on a subject's head and having the subject wear the apparatus during sleep, and providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms, wherein the low dose electrical current is provided at 2 milli-amps (mA), and a 33% duty cycle.

Still another embodiment of the present invention includes a method of providing therapy for movement disorder symptoms comprising steps of providing a wearable apparatus, inserting, attaching to, affixing to, or embedding in the wearable apparatus an array of at least five surface scalp electrodes, at least one central anodal electrode surrounded by at least four return electrodes arranged in a ring around the anodal electrode, placing the apparatus on a subject's head and having the subject wear the apparatus during sleep, and providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms, wherein the low dose electrical current is provided at 2 milli-amps (mA).

Still yet another embodiment of the present invention includes a movement disorder therapy device comprising a wearable apparatus capable of being worn about a subject's head, at least two surface scalp electrodes affixed to or embedded in the wearable, at least one electrode for providing a low dose direct electrical current to the patient, and at east one electrode for return of the low dose direct electrical current, a processor comprising a stimulation control program for controlling how the low dose electrical current is provided to the patient, and a current generator for providing a low-dose (low current) electrical stimulation impulse through the at least one electrode for providing a low dose direct electrical current to the patient, wherein the current generator is capable of providing a steady, constant current at a predetermined duty cycle.

Even yet another embodiment of the present invention includes a movement disorder therapy device comprising a wearable apparatus capable of being worn about a subject's head, an array of at least five surface scalp electrodes, at least one central anodal electrode surrounded by at least four return electrodes arranged in a ring around the anodal electrode, a processor comprising a stimulation control program for controlling how the low dose electrical current is provided to the patient, and a current generator for providing a low-dose (low current) electrical stimulation impulse through the at least one electrode for providing a low dose direct electrical current to the patient, wherein the current generator is capable of providing a steady, constant current at a predetermined duty cycle.

Still another embodiment of the present invention includes a movement disorder therapy device comprising a wearable apparatus capable of being worn about a subject's head, an array of at least five surface scalp electrodes, at least one central anodal electrode surrounded by at least four return electrodes arranged in a ring around the anodal electrode, a processor comprising a stimulation control program for controlling how the low dose electrical current is provided to the patient, and a current generator for providing a low-dose (low current) electrical stimulation impulse through the at least one electrode for providing a low dose direct electrical current to the patient, wherein the current generator is capable of providing a steady, constant current at a predetermined 33% duty cycle.

Yet another embodiment of the present invention includes a movement disorder therapy device comprising a harness to be worn about a subject's head, an electrode array comprising at least five surface scalp electrodes, at least one anodal electrode for delivering a low dose constant electrical current and at least for return electrodes for the current to exit the subject, and a current generator wherein the surface area of each the electrodes in contact with the subject's skin is 8 mm or less, and wherein the current generator is capable of supplying a constant current according to a predetermined 50% duty cycle.

Even still yet another embodiment of the present invention includes a method of providing therapy for movement disorder symptoms comprising steps of placing an apparatus comprising a flexible harness and an array of at least 5 surface scalp electrodes, at least one electrode, applying a constant direct current at about 2 mA (milli-amps) transcranially to a subject's brain at a 33% duty cycle, wherein the current is active for at least thirty (30) minutes continuously during each cycle, and wherein the apparatus is placed on the subject's head in a manner to align the electrodes to deliver the current to a portion of the subject's brain corresponding to a desired movement disorder symptom to be treated.

Still even yet another embodiment of the present invention includes a method of providing therapy for movement disorder symptoms comprising steps of providing a wearable apparatus, providing an array of at least five surface scalp electrodes, at least one central anodal electrode surrounded by at least four return electrodes arranged in a ring around the anodal electrode, affixing or embedding the electrode array to the wearable apparatus, placing the apparatus on a subject's head and having the subject wear the apparatus during sleep, checking the electrical impedance of each of the at least five electrodes, and providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms, wherein the low dose electrical current is provided at about 2 milli-amps (mA).

Yet another embodiment of the present invention includes a method of providing therapy for movement disorder symptoms comprising steps of providing a wearable apparatus, providing a wearable apparatus comprising at least two surface scalp electrodes, at least one electrode for providing a low dose direct electrical current to the patient, and at least one electrode for return of the low dose direct electrical current, affixing or embedding the electrode array to the wearable apparatus, placing the apparatus on a subject's head and having the subject wear the apparatus during sleep, checking the electrical impedance of each of the at least five electrodes, and providing a low dose direct electrical current from the at least one surface scalp electrode for providing a low dose direct electrical current across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms, wherein the low dose electrical current is provided at about 2 milli-amps (mA).

Even still yet another embodiment of the present invention includes a method of providing therapy for movement disorder symptoms comprising steps of custom fitting a wearable apparatus to fit a subject's head, providing an array of at least five surface scalp electrodes, at least one central anodal electrode surrounded by at least four return electrodes arranged in a ring around the anodal electrode, affixing or embedding the electrode array to the custom-fitted wearable apparatus, placing the apparatus on a subject's head and having the subject wear the apparatus during sleep, checking the electrical impedance of each of the at least five electrodes, and providing a low dose direct electrical current from the at least one surface scalp electrode for providing a low dose direct electrical current across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms.

Even still another embodiment of the present invention includes a method of providing therapy for movement disorder symptoms comprising steps of providing a wearable apparatus, providing an array of at least five surface scalp electrodes, at least one central anodal electrode surrounded by at least four return electrodes arranged in a ring around the anodal electrode, affixing or embedding the electrode array to the wearable apparatus, placing the apparatus on a subject's head and having the subject wear the apparatus during sleep, determining the subject's sleep stage substantially in real time, and providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement and/or sleep disorder symptoms, wherein the duty cycle for providing the low dose direct electrical current is turned on based at least in part on the determined sleep stage.

Still even another embodiment of the present invention includes a method of providing therapy for movement disorder symptoms comprising steps of custom fitting a wearable apparatus to fit a subject's head, providing an array of at least five surface scalp electrodes, at least one central anodal electrode surrounded by at least four return electrodes arranged in a ring around the anodal electrode, affixing or embedding the electrode array to the custom-fitted wearable apparatus, placing the apparatus on a subject's head and having the subject wear the apparatus during sleep, determining the subject's sleep stage substantially in real time, and providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement and/or sleep disorder symptoms, wherein the duty cycle for providing the low dose direct electrical current is turned on based at least in part on the determined sleep stage.

Yet still another embodiment of the present invention includes a method of providing therapy for movement disorder symptoms comprising steps of providing a wearable apparatus, providing a wearable apparatus comprising at least two surface scalp electrodes, at least one electrode for providing a low dose direct electrical current to the patient, and at least one electrode for return of the low dose direct electrical current, affixing or embedding the electrode array to the wearable apparatus, placing the apparatus on a subject's head and having the subject wear the apparatus during sleep, determining the subject's sleep stage substantially in real time, and providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement and/or sleep disorder symptoms, wherein the duty cycle for providing the low dose direct electrical current is turned on based at least in part on the determined sleep stage.

Still even yet another embodiment of the present invention includes a method of providing therapy for movement disorder symptoms comprising steps of providing a wearable apparatus, providing an array of at least five surface scalp electrodes, at least one central anodal electrode surrounded by at least four return electrodes arranged in a ring around the anodal electrode, affixing or embedding the electrode array to the wearable apparatus, placing the apparatus on a subject's head and having the subject wear the apparatus during sleep, checking the electrical impedance of each of the at least five electrodes, determining the subject's sleep stage substantially in real time, and providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement and/or sleep disorder symptoms, wherein the duty cycle for providing the low dose direct electrical current is turned on based at least in part on the determined sleep stage.

Yet another embodiment of the present invention includes a method of providing therapy for movement disorder symptoms comprising steps of providing a wearable apparatus, providing a wearable apparatus comprising at least two surface scalp electrodes, at least one electrode for providing a low dose direct electrical current to the patient, and at least one electrode for return of the low dose direct electrical current, affixing or embedding the electrode array to the wearable apparatus placing the apparatus on a subject's head and having the subject wear the apparatus during sleep, checking the electrical impedance of each of the at least five electrodes, determining the subject's sleep stage substantially in real time, and providing a low dose direct electrical current from the at least one anodal electrode across the subject's cranium to stimulate at least one area of the subject's brain at a predetermined duty-cycle, the area of the subject's brain being stimulated corresponding to at least one symptom of a movement disorder to reduce the occurrence, severity, and/or duration of movement and/or sleep disorder symptoms, wherein the duty cycle for providing the low dose direct electrical current is turned on based at least in part on the determined sleep stage.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. It is understood that many other embodiments of the invention are not directly set forth in this application but are none the less understood to be incorporated by this application. The accompanying drawings are included to provide a further understanding of the invention, and are incorporated in and constitute a part of this specification. The drawings illustrate various embodiments of the invention and together with the with the description serve to explain the principles and operation of the many embodiments of this invention.

DETAILED DESCRIPTION OF THE PREFERRED EMBODIMENTS

Figure 1:
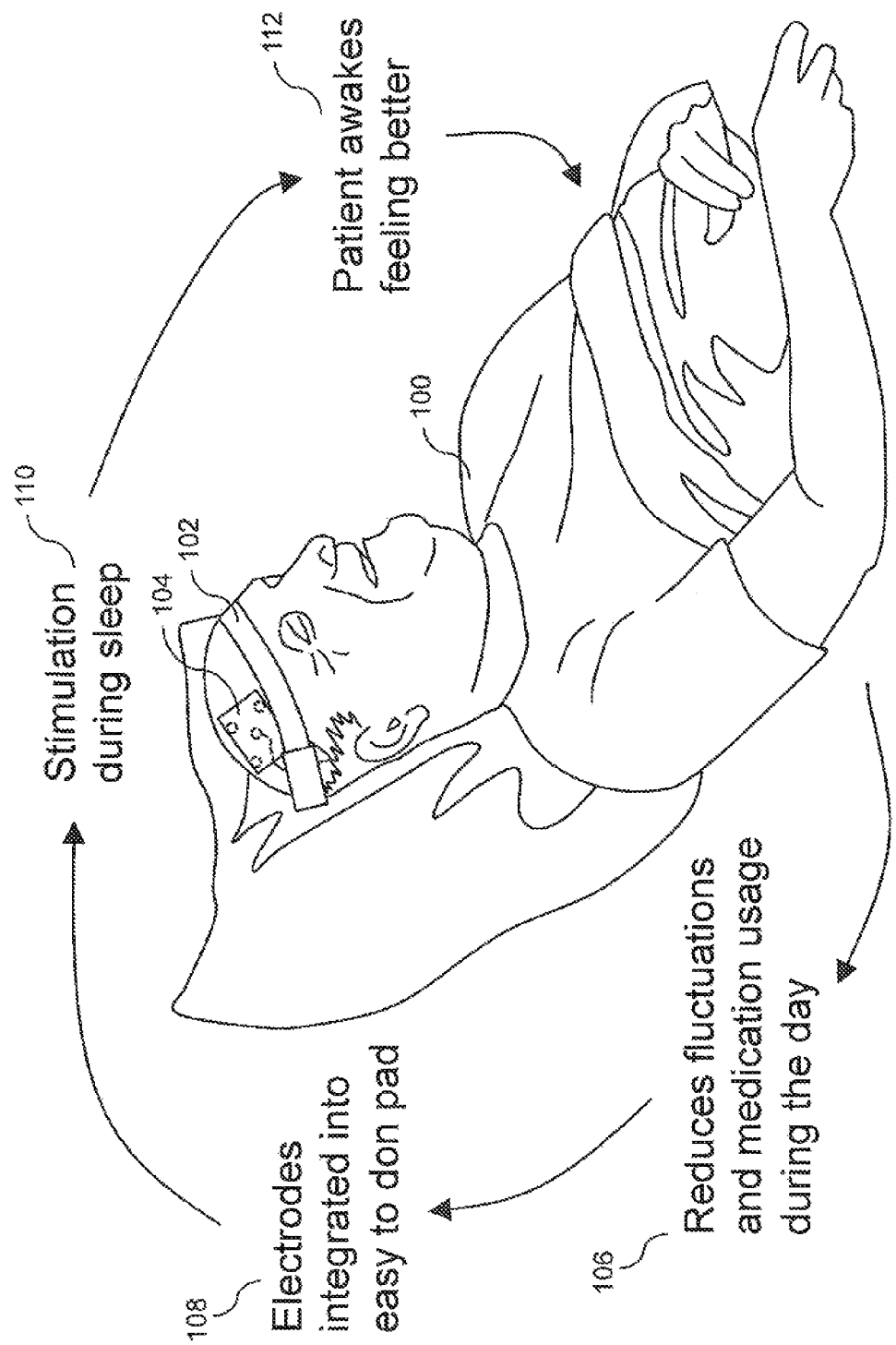
FIG. 1. is a diagram of a subject wearing one embodiment of the invention and receiving tDCS therapeutic treatment while asleep.

The present invention relates to a system and methods for noninvasively providing therapy for movement disorder symptoms. Movement disorders, for the purposes of this invention, include, but are not limited to, Parkinson's Disease and Parkinsonism, Dystonia, Cerebral Palsy, Chorea and dyskinesias in general, Huntington's Disease, Ataxia, Tremor and Essential Tremor, Myoclonus, tics, Tourette Syndrome, Restless Leg Syndrome, Stiff Person Syndrome, gait disorders, sleep disturbances, and the like. The present invention provides such a therapy system which provides trans-cranial direct current stimulation (tDCS) in order to treat those symptoms and the disorders. The present invention further provides such tDCS therapy while the subject sleeps in order to minimize the time required and impact of the therapy on the subject's waking life. The system, methods, and devices of the present invention are intended to provide a low-dose electrical current, trans-cranially, to a specific area of the subject's brain while he or she sleeps in order to decrease the occurrence, severity, and duration of the symptoms of movement disorders. The present invention aims to reduce the amount of medication necessary, counteract the effects of medication wearing off during sleep, and to overall improve the quality of life of subjects suffering from movement disorders.

For the present invention the subject who is receiving therapy for movement disorder symptoms can be any type of animal, preferably a mammal, most preferably a human. The subjects for whom the device is utilized are identified by a diagnosis of a movement disorder and exhibiting of symptoms thereof. The device and methods are designed to be used and performed, respectively, largely by untrained or minimally trained personnel, and most preferably by the subject himself or herself with very little instruction, and no formal education required.

The devices and methods of the present invention are designed to be used and performed at home. The present invention is designed so as the subject or patient can use the devices and methods with no formal training or education, and with little or no special training required. The present invention is preferably used by the subject or patient outside of a clinical setting. The present invention is designed to be small, lightweight, portable, and rugged, and thus capable of being used in the subject's home or while travelling. Many embodiments of the present invention involve the subject or patient using the devices and methods during sleep, thus the system is specifically designed to be used daily in the subject's or patient's normal course of life without requiring bulky, cumbersome equipment, special facilities, or access to medical personnel.

The system preferably operates substantially in real time. By real-time, it is intended that the system acquires any signals and makes any required calculations or determinations based on those signals in less than 5 minutes. More preferably, the system performs these functions in less than 3 minutes. Even more preferably, the system performs these functions in less than 1 minute. Still more preferably, the system performs these functions in less than 45 seconds. Yet more preferably, the system performs these functions in less than 30 seconds. Even still more preferably, the system performs these functions in less than 20 seconds. Still yet more preferably, the system performs these functions in less than 10 seconds. Even still yet more preferably, the system performs these functions in less than 5 seconds. Most preferably, the system performs these functions substantially simultaneously.

Various embodiments of the methods of the present invention include one or more of the following steps, and variations thereof. These steps include, but are not limited to, providing a wearable apparatus comprising at least two surface scalp electrodes, at least one electrode for providing a low dose direct electrical current to the subject, and at least one electrode for return of the low dose direct electrical current, placing the apparatus on a subject's head and having the subject wear the apparatus during sleep, and providing a low dose direct electrical current from the at least one surface scalp electrode for providing a low dose direct electrical current across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms.

Similarly, various embodiments of the present invention include one or more of the following components, and variations thereof. These components include, but are not limited to, a wearable apparatus capable of being worn about a subject's head, at least two surface scalp electrodes affixed to or embedded in the wearable, at least one electrode for providing a low dose direct electrical current to the subject, and at least one electrode for return of the low dose direct electrical current, an array of at least five surface scalp electrodes, at least one central anodal electrode surrounded by at least four return electrodes arranged in a ring around the anodal electrode, a processor comprising a stimulation control program for controlling how the low dose electrical current is provided to the subject, and a current generator for providing a low-dose (low current) electrical stimulation impulse through the at least one electrode for providing a low dose direct electrical current to the subject.

The first step in utilizing all embodiments of the present invention is identifying a subject or patient for whom tDCS therapy would be beneficial. Subjects or patients who are or have been experiencing symptoms of movement disorders, or who have been diagnosed with a movement disorder may be selected to use the present invention's devices and methods. Additionally, subjects or patients with symptoms or diagnoses of some mental health disorders (e.g., depression, anxiety disorders, schizophrenia, obsessive compulsive disorder, and the like), or other disorders (e.g., tinnitus, fibromyalgia, speech difficulties, memory and cognitive issues, and the like), would be valid candidates for using the present invention. Typical movement disorders and symptoms sought to be treated by the present invention include, but are not limited to, Parkinson's Disease and Parkinsonism (characterized by shaking, rigidity, slow movement, gait disturbances, cognitive and behavioral decline, sleep disturbances, etc.), Dystonia (sustained muscle contractions and torsion), Cerebral Palsy (characterized by abnormal muscle tone, abnormal reflexes, motor coordination decline, spasms and involuntary movements, gait and balance issues, etc.), Bradykinesia (slowness of movement), Chorea and dyskinesias in general (characterized by rapid, involuntary movements of the body), Huntington's Disease (characterized by lack of coordination, dyskinesias, rigidity, loss of cognitive capacity, and the like depending on the disease's progression), Ataxia (gross lack of coordination), Tremor and Essential Tremor (involuntary muscle contraction and relaxing), Myoclonus (brief, involuntary muscle twitching), tics (motor and phonic tics), Tourette Syndrome (characterized by multiple motor tics and phonic tic(s)), Restless Leg Syndrome (irresistible urge to move the body to do uncomfortable sensations), Stiff Person Syndrome (progressive rigidity and stiffness, spasms), gait disorders, sleep disturbances (as a result of some other movement or mental health disorder), and the like. The symptoms for many of the above disorders, particularly the movement disorders, tend to overlap between disorders, and often stand alone as their own disorder (e.g., Bradykinesia). Subjects or patients who experience any of the above or similar symptoms, or are diagnosed with any of these, or similar disorders, can be selected as viable beneficiaries of tDCS therapy. Further, subjects who are currently on medication for one or more of the symptoms or disorders may benefit from tDCS therapy. Some preferred embodiments of the present invention are aimed at treating subjects with symptoms and/or diagnoses of movement disorders, such as Parkinson's Disease, Tremor and Essential Tremor, Huntington's Disease, and the like.

All embodiments of the present invention are designed to help improve the subject's quality of life by reducing the occurrence, severity, and/or duration of the symptoms of his or her particular disorder(s). Improvement should be measured by each individual symptom as a single subject may exhibit multiple symptoms from a single or multiple disorders. Improvement may be measured as a reduction in the particular symptom (e.g., % reduction in the occurrence of dyskinesias), or by the increase in subject's functionality (e.g., % increase in motor response time). The nature of tDCS therapy typically requires individual symptoms to be treated separately, as each symptom is typically controlled or triggered by a different part of the brain. The subject and his or her physician typically, during the screening process, determine which symptom(s) are the most troublesome to the subject's life and design the therapy to treat those symptoms. Regardless of which symptom(s) are being treated (i.e., motor/physical symptoms or mental health symptoms), the present invention is designed to improve the subject's quality of life by reducing the occurrence, severity, and/or duration of symptoms. Preferably, the subject experiences at least a 3% improvement in symptom occurrence, severity, and/or duration. More preferably, the subject experiences at least a 5% improvement in symptom occurrence, severity, and/or duration. Still more preferably, the subject experiences at least a 10% improvement in symptom occurrence, severity, and/or duration. Yet more preferably, the subject experiences at least a 13% improvement in symptom occurrence, severity, and/or duration. Even more preferably, the subject experiences at least a 15% improvement in symptom occurrence, severity, and/or duration. Even still more preferably, the subject experiences at least a 20% improvement in symptom occurrence, severity, and/or duration. Still yet more preferably, the subject experiences at least a 23% improvement in symptom occurrence, severity, and/or duration. Even yet more preferably, the subject experiences at least a 25% improvement in symptom occurrence, severity, and/or duration. Still even more preferably, the subject experiences at least a 27% improvement in symptom occurrence, severity, and/or duration. Even still yet more preferably, the subject experiences at least a 30% improvement in symptom occurrence, severity, and/or duration. Most preferably, the subject experiences a greater than 35% improvement in symptom occurrence, severity, and/or duration.

Improvement in symptoms, particularly for movement disorders, and even more particularly for Parkinson's Disease and its associated symptoms, may be quantitatively measured by means of a reduction in symptom scoring according to scoring methods and systems known to those in the art. Examples of such scoring systems include the UPDRS, MDS-UPDRS. Another such scoring method for quantifying movement disorder symptoms, similar to these two systems, is presented in U.S. patent application Ser. No. 13/152,963, which is herein incorporated by reference. These systems for scoring movement disorder symptoms provide a score that relates to the severity of the symptom. Typically, the higher the score, the more severe the symptom. If UPDRS or MDS-UPDRS scores are used, a clinician typically monitors the progression of the symptoms. However, the system in application Ser. No. 13/152,963 allows for automated or semi-automated scoring at home. That system can be utilized with the present invention to quantify symptoms, treat them with tDCS therapy, and track the progression or improvement of those symptoms. Regardless of the scoring method that is actually used, the present invention aims to provide an improvement in the subject's or patient's symptoms as measured by one of these scoring systems. The UPDRS is, at the time of this application, the most commonly known and used scoring system, and, therefore preferably, the subject experiences at least a 10% reduction in UPDRS score for at least one symptom. More preferably, the subject experiences at least a 20% reduction in UPDRS score for at least one symptom. Still more preferably, the subject experiences a 30% reduction in UPDRS score for at least one symptom. Yet more preferably, the subject experiences at least a 40% reduction in UPDRS score for at least one symptom. Even more preferably, the subject experiences at least a 50% reduction in UPDRS score for at least one symptom. Still yet more preferably, the subject experiences at least a 60% reduction in UPDRS score for at least one symptom. Even yet more preferably, the subject experiences at least a 70% reduction in UPDRS score for at least one symptom. Even yet more preferably, the subject experiences at least a 80% reduction in UPDRS score for at least one symptom. Even still yet more preferably, the subject experiences a at least 90% reduction in UPDRS score for at least one symptom.

Recent studies have shown that tDCS therapy shows noticeable improvement in movement disorder symptoms when compared to sham stimulation. See David H. Benninger et al. *Transcranial Direct Current Stimulation for the Treatment of Parkinson's Disease,* 81 J. NEUROL. NEUROSURG. PSYCHIATRY 1105 (2011); see also Felipe Fregni, MD, PhD et al., *Noninvasive Cortical Stimulation with Transcranial Direct Current Stimulation in Parkinson's Disease,* 21 MOVEMENT DISORDERS 1693 (2006). Sham stimulation is a control condition wherein a brief electrical impulse is delivered to the subject to imitate the initiation of tDCS therapy, but the current is then shut off for the rest of the stimulation time. By using tDCS, it is possible to show measurable, significant improvement in individual movement disorder symptoms.

For gait abnormalities or disturbances, the more often, severe, or length the disturbance, the longer it takes the subject to walk a given distance. Thus, one way to measure improvement in gait disturbances is by showing a decrease in walking time over a given distance. By using the present invention to treat gait abnormalities or disturbances, preferably the subject experiences at least a 15% decrease in walking time. More preferably, the subject experiences at least a 20% decrease in walking time. Yet more preferably, the subject experiences at least a 25% decrease in walking time. Still more preferably, the subject experiences at least a 30% decrease in walking time. Even more preferably, the subject experiences at least a 35% decrease in walking time. Still yet more preferably, the subject experiences at least a 40% decrease in walking time. Even yet more preferably, the subject experiences at least a 45% decrease in walking time. Even still more preferably, the subject experiences a greater than 50% decrease in walking time.

For bradykinesia, or slowness of movement, improvement can be shown by measuring the length of time it takes for the subject to complete a series of sequential movements, and having that sequential movement time decrease. By using the present invention to treat bradykinesia, preferably the subject experiences at least a 25% decrease in sequential movement time. More preferably, the subject experiences at least a 30% decrease in sequential movement time. Yet more preferably, the subject experiences at least a 35% decrease in sequential movement time. Still more preferably, the subject experiences at least a 40% decrease in sequential movement time. Even more preferably, the subject experiences at least a 45% decrease in sequential movement time. Still yet more preferably, the subject experiences at least a 50% decrease in sequential movement time. Even still more preferably, the subject experiences at least a 55% decrease in sequential movement time. Even yet more preferably, the subject experiences a greater than 60% decrease in sequential movement time.

Improvement in tremor and Essential tremor, the involuntary contraction and relaxing of muscles appearing as oscillations or twitching of the subject's body, particularly the extremities, can be measured or quantified by a reduction the frequency (number of oscillations or twitches per second) of the tremor. This is not the same as how often tremor occurs, but rather an actual measurement of the tremor when it does occur. Essentially, improvement in tremor appears as a slowing of the oscillations or twitches, with the aim of reducing the frequency enough to allow the subject to feel and appear still and steady. Through using the present invention, the subject preferably experiences at least a 10% reduction in the tremor frequency. More preferably, the subject preferably experiences at least a 20% reduction in the tremor frequency. Yet more preferably, the subject preferably experiences at least a 30% reduction in the tremor frequency. Still more preferably, the subject preferably experiences at least a 40% reduction in the tremor frequency. Even more preferably, the subject preferably experiences at least a 50% reduction in the tremor frequency. Still yet more preferably, the subject preferably experiences at least a 60% reduction in the tremor frequency. Even yet more preferably, the subject preferably experiences at least a 70% reduction in the tremor frequency. Even still more preferably, the subject preferably experiences at least a 80% reduction in the tremor frequency. Even still yet more preferably, the subject preferably experiences a greater than 90% reduction in the tremor frequency.

The step of providing a wearable apparatus comprising at least two surface scalp electrodes, at least one electrode for providing a low dose direct electrical current to the subject, and at least one electrode for return of the low dose direct electrical current is the first step in many method embodiments of the present invention. In order to provide therapy to a subject via tDCS, the appropriate mechanism and/or apparatus must be applied to the subject's head. The present invention may utilize various forms of this wearable apparatus in various embodiments. Preferably, the wearable apparatus is designed to be flexible, easy to don and doff, and disposable yet still resilient and capable of withstanding forces common in daily wear, wear during sleep, and even emergency settings. In some embodiments, the wearable may be a custom fitted wearable that is molded, formed, or otherwise constructed to individually fit each specific subject. The custom fitted wearable allows for easy, repeatable placement of the electrodes (described in greater detail below) in the proper location(s). In embodiments where the wearable device is a custom-molded head-worn apparatus, the apparatus itself should be capable of being worn daily for a long period of time (on the order of years), without being damaged or worn out. Further, in such custom molded embodiments, the electrodes or array(s) may be affixed to or embedded into the wearable apparatus by the subject before donning the head worn apparatus, and discarded each morning, or replaced periodically. Alternatively, the wearable apparatus may be non-custom fitted in the sense that it may be of a uniform size, shape, and/or configuration for all subjects. In such embodiments, the patient is preferably trained or otherwise instructed on the proper method and location of placing the wearable to ensure the electrodes are in the proper location and configuration to provide the therapy.

The wearable being provided may be constructed of any material known to those of skill in the art. Preferably, the wearable is designed and constructed to be durable, resilient, flexible, and easy to clean. The apparatus may be secured about the subject's head by means commonly known to those in the art, including, but not limited to, a cap or other garment completely encompassing the subject's head, a strap that is secured by compression or elastic means, or may utilize common fastening methods such as hook-and-loop, belt-type, snap connectors, or the like. Additionally, or in conjunction with one of the above means, an adhesive layer may be used with a wearable apparatus to further ensure a stable, secure placement of the electrode lead or array. In embodiments where the electrodes are affixed to or embedded in a disposable patch-like wearable, the adhesive layer is particularly important to maintain secure, stable placement of the electrodes on the subject's head. In a preferred embodiment, the head-worn apparatus is a custom molded cap that fits snugly but comfortably about the subject's head, and is capable of maintaining a secure placement with minimal shifting, drift, or other movement of the apparatus, for the entire length of time necessary for monitoring. The adhesive layer is also preferably capable of providing a secure, stable attachment to the subject in the presence of dirt, sweat, and other detritus which may be covering the subject's skin during application, without the need for washing, cleaning or otherwise preparing the area of application.

The step of placing the apparatus on a subject's head and having the subject wear the apparatus during sleep refers to a preferred embodiment wherein the patient wears the device and receives tDCS therapy during sleep. The wearable is preferably applied to the subject's head in a manner such that the electrodes come into contact with the subject's skin. The wearable is placed onto the subject's head, and is then secured by virtue of one of the above listed, or similar means, in order to ensure secure, stable positioning of the wearable and thus the electrodes during use. Preferably, the location where the electrodes come in contact with the subject's skin checked and found to be free from cuts, lesions, skin disease, and other skin irritations which can impair the connection and attachment of the electrodes to the subject's skin.

In some embodiments, including a preferred embodiment, the system preferably includes a step of measuring electrical impedance of the electrodes. Impedance checking is used to ensure that the electrodes have good contact with the subject's skin. Good electrode-skin contact ensures accurate, efficient delivery of the tDCS current, and thus maximizes the effectiveness of the therapy. Impedance checking can be done in several ways.

The system may perform electrical impedance checking by any method currently known to those in the art or later developed. One such method of electrode impedance measurement involves calculating the electrical impedance value by measuring a voltage across two electrodes. The two electrodes may each be signal measurement or current delivery electrodes (again, the electrodes are described in greater detail below), or may be a measurement or delivery electrode and a reference or return electrode. Impedance is the complex form of electrical resistance, that is, impedance is the electrical resistance to sinusoidal alternating current (AC). Impedance values take on a complex form containing both a magnitude as well as a phase, which indicates the lag between the current and voltage. Impedance can be calculated as a function of both the magnitudes and the phases of the voltage, current, and impedance. In various embodiments of the present invention, the calculation is very similar to traditional Ohm's law and calculates impedance by dividing the measured voltage by the known current. The phase component describes the fraction of the lagging wave that has been completed by the when it reaches the same reference point as the first signal, in the present case that reference point is the electrode. The calculation of an electrode's impedance involves supplying an electrical current to the electrode at a known frequency and amplitude, and measuring the voltage across that electrode and another electrode. In the first step, an electrical current is supplied to the first electrode. Once the current is being applied at the known frequency and amplitude, the system is able to take the required voltage measurement across the current-supplied electrode and another electrode, and calculate the impedance of that electrode to which the current is applied. Thereafter, the process is repeated for the other electrodes to get impedance measurements for each of them. Some embodiments may involve simultaneously supplying a current at a known amplitude and frequency to two electrodes, and measuring the voltage, thus providing a total impedance for the two electrodes combined. In such embodiments, the first electrode's calculated impedance is subtracted from the total impedance of the two electrodes to obtain the second electrode's impedance value. In many other embodiments; however, the impedance values are measured individually for each electrode by supplying a current to each electrode in turn, as described above. In embodiments utilizing an electrode array, such as the previously described 4×1 array, the electrodes in each array are typically and preferably employed as a single electrode, or rather a single device. In such embodiments, the electrodes may be individually addressable, but are more often a single passive device wherein there is a single anodal electrode and the cathode is divided into separate parts, for example 4 parts in the 4×1 array. For purposes of the electrode impedance measurement described above with electrode array embodiments, when two electrodes are used, typically, such impedance measurements are performed between and/or among two separate arrays, and not between and/or amongst individual electrodes in a single array.

Given the nature of tDCS therapy as applied by the current invention, a preferred embodiment involves carrying out the above impedance measurement process during the period of the duty cycle in which no therapeutic current is applied to the subject. This allows the therapeutic current to be applied for the entire desired period without interruption to measure electrode impedance. In order to ensure that electrode impedance is as low as possible, and thus the connection between the electrodes and the subject's skin is as strong as possible, the impedance measurement is preferably taken as close in time to the duty cycle on-period as possible. That is, preferably, the electrode impedance measurement is taken less than 10 minutes before the therapeutic tDCS current is turned on. More preferably, the electrode impedance measurement is taken less than 8 minutes before the therapeutic tDCS current is turned on. Still more preferably, the electrode impedance measurement is taken less than 6 minutes before the therapeutic tDCS current is turned on. Even more preferably, the electrode impedance measurement is taken less than 4 minutes before the therapeutic tDCS current is turned on. Yet more preferably, the electrode impedance measurement is taken less than 2 minutes before the therapeutic tDCS current is turned on. In the event that the impedance measurement of an electrode is too high, the system may provide a warning to the subject to wake up and replace the electrode, may alert another person to change the electrode, may divert the current away from that electrode and only using the remaining electrodes, and/or may halt the duty cycle on-period from beginning until the electrode impedance can be fixed.

Once the wearable is properly situated and secured onto the subject's head, and the impedance of each of the electrodes is at an acceptable level, the step of providing a low dose direct electrical current from the at least one surface scalp electrode for providing a low dose direct electrical current across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms, can begin. In this step, a current generator begins to supply a direct current at a known, steady amperage, through at least one electrode, across the subject's cranium, and into the brain. This current is preferably targeted at a particular area of the subject's brain which corresponds to the occurrence of movement disorder symptoms. For example, using the direct electrical current to stimulate the basal ganglia may have a positive effect in reducing bradykinesia. The method by which the current is applied depends largely on the type of electrodes used. Traditional tDCS systems used in laboratory settings typically use a large (e.g. 25-35 cm$^2$) saline-soaked sponge electrodes which are not practical for home use. Another option is to use a still relatively large (e.g., 5×7 cm) electrode pad; however, these large electrode pads may increase scalp temperature causing discomfort to the subject, and typically result in current being concentrated around the edges of the electrode pad, and thus less accurately delivered to a targeted brain area.

All embodiments of the present invention will utilize electrodes. The electrodes used may be any of those commonly known in the art of tDCS and EEG monitoring. The electrodes preferably do not require the application of conductive paste or gel. Therefore, the electrode lead or array preferably has any necessary conductive fluids pre-applied. Even more preferably, the electrodes are dry physiological electrodes requiring no conductive fluid at all. Dry physiological recording electrodes of the type described in U.S. Pat. No. 6,785,569 can be used. U.S. Pat. No. 6,785,569 is hereby incorporated by reference. Dry electrodes provide the advantage that there is no gel to dry out, no skin to abrade or clean, and that the electrode can be applied in hairy, sweaty, and/or dirty areas such as the scalp, particularly for in-the-field applications. The electrode lead or array may be affixed to or embedded into a flexible, wearable apparatus which can be applied directly to the subject's head at the desired location, as discussed above.

In some embodiments, least two surface scalp electrodes affixed to or embedded in the wearable, at least one electrode for providing a low dose direct electrical current to the subject, and at least one electrode for return of the low dose direct electrical current, are provided. Typically for tDCS, such electrodes are placed on opposite sides of the subject's head. As such, one electrode is used to provide the current directly across the subject's cranium, through the brain, and is drawn out the other side through the return electrode. However, the present invention may utilize a two electrode configuration wherein the two electrodes are applied near each other, on the same side of the subject's head, thus supplying the current to the desired brain location and drawing it out the same side. Preferably, the anodal electrode is positioned in such a manner so as to deliver the therapeutic current to the patient's primary motor cortex (C3 or C4) contralateral to the more effected side.

Some embodiments may employ a dual stimulation approach wherein both anodal and cathodal stimulation are provided simultaneously. Anodal stimulation increases the excitability of the targeted region whereas cathodal stimulation tends to decrease such excitability. In such embodiments, the anodal stimulation is still provided to the region of the subject's brain that corresponds to the particular symptom(s) which are being targeted. Cathodal stimulation, however, is supplied to the unaffected portion of the brain that is the counterpart to the affected region, or corresponds to the other side of the subject which is not symptomatic. In other words, anodal stimulation increases the excitability of the portion of the brain giving rise to the movement disorder symptoms, and cathodal stimulation decreases the excitability of the counterpart regions which do not correspond to symptoms. In typical tDCS therapy, there is always an anode and a cathode, though typically the cathode is placed in an area where it provides no stimulation to the brain, but merely serves to draw the electrical current out along a safe path. In embodiments using the dual stimulation method, the cathode is placed in a location so as to provide stimulation to the subject's brain as described above. Such dual stimulation may be performed simultaneously, according to the same duty cycle. In such embodiments, the affected and unaffected sides would receive anodal and cathodal stimulation, respectively, at the same time, and such stimulation would be turned on and off at the same time according to the same duty cycle.

In other, more preferred embodiments, an array of at least five surface scalp electrodes is supplied. In such embodiments, all at least five electrodes are applied on the same side of the subject's head. The at least five electrodes may be individual, or may be affixed to or embedded into a patch or similar apparatus for keeping the electrodes in a stable arrangement with respect to each other. In many embodiments, the electrodes may preferably each be individually addressable, and able to be be removed and replaced individually without affecting the other electrodes in the array. In light of the description of a wearable apparatus above, it is preferably possible to remove and/or insert an individual electrode into the wearable. Some embodiments may utilize a combination of these features wherein the electrodes are affixed to or embedded individually into a patch-like apparatus, and wherein said patch is then inserted into the wearable which is applied to the subject's head, thus maintaining individual addressability of the electrodes and making it easier to replace the electrode array on a periodic basis.

In a preferred embodiment, the electrodes provided are small electrodes provided in an array. Preferably, in such embodiments, the electrodes are arranged in a 4×1 ring array. By this, it is meant that there is at least one central anodal electrode surrounded by at least four return electrodes arranged in a ring around the anodal electrode. The central anodal electrode is used to supply the direct current to the subject's brain, and the four return electrodes arranged around the central anodal electrode are used to draw the current back out of the brain. Such arrangement is preferred because it has been shown to not significantly raise scalp temperature, nor to modulate cortex in undesired regions. This helps to minimize the subject's discomfort and to more efficiently effect the desired therapy on the subject. Preferably, the small electrodes are as described above: either pre-applied with gel, or more preferably, dry electrodes requiring no conductive gels or pastes at all. By small, it is meant that the electrodes are preferably less than 3 cm in diameter. More preferably, the electrodes are less than 2.5 cm in diameter. Even more preferably, the electrodes are less than 2 cm in diameter. Still more preferably, the electrodes are less than 1.5 in diameter. Yet more preferably, the electrodes are less than 1 cm in diameter. Still yet more preferably, the electrodes are less than 8 mm in diameter. Even still more preferably the electrodes are less than 5 mm in diameter. Another way to describe the electrode size for use with the present invention is in regards to surface area. Preferably, the electrodes have a surface area that is less than 8 $cm^2$. More preferably, the electrodes have a surface area that is less than 5 $cm^2$. Yet more preferably, the electrodes have a surface area that is less than 4 $cm^2$. Still more preferably, the electrodes have a surface area that is less than 2 $cm^2$. Even more preferably, the electrodes have a surface area that is less than 1 $cm^2$. Still yet more preferably, the electrodes have a surface area that is less than 75 $mm^2$. Even yet more preferably, the electrodes have a surface area that is less than 50 $mm^2$. Even still more preferably, the electrodes have a surface area that is less than 25 $mm^2$.

Another element of all embodiments of the present invention is a processor comprising a stimulation control program for controlling how the low dose electrical current is provided to the subject. The processor can be any type of computer or controller suitable to comprise and run a control program for the current generator. Preferably the process is small in that it does not take up large amount of space, and can be easily stored, and kept relatively inconspicuously near the subject while he or she sleeps. Preferably, the processor is a microprocessor that can be integrated into other hardware this minimizing the size of the device. Further preferably, the entire device is miniaturized and thus portable, so the subject is able to easily transport the device for use while travelling or otherwise away from home.

The stimulation control program is the program that controls the desired duty cycle for the therapeutic electrical current. The control program may be tailored and custom-programmed for each subject based on his or her particular movement disorder, symptoms, and other physiological or other concerns. The stimulation control program may further determine when to initiate the on-period of the duty cycle based on real-time subject specific parameters. For example, the duty cycle may be controlled based at least on part on the subject's sleep stage. In such embodiments, the system may detect the patient's sleep stage and then determine when to initiate therapy. Typically, sleep stages are separated into two major categories: rapid eye movement (REM), and non-REM sleep. The non-REM stage is further subdivided into as many as four separate categories: Stage 1, characterized by theta activity of high amplitude, slow moving brain waves (typically between 3.5-7.5 Hz) which is between wakefulness and sleep; Stage 2, characterized by the beginning of rapid, rhythmic brain activity known as sleep spindles; Stage 3, characterized by the onset of delta activity of deep, slow brain waves; and Stage 4, characterized by further, sustained delta wave activity. REM activity, or deep sleep characterized by increased brain activity and rapid eye movement, is the fifth stage and follows Stage 4. With regard to the stimulation control program, the system may initiate therapy when the patient any of these stages of sleep, though preferably at least waits until stage 2 at which point the patient is actually considered to be asleep. In such embodiments, the duty cycle may then be controlled on a strict time period basis where the current is on for a predetermined amount of time, and then off for a separate predetermined time period. Alternatively, once therapy is initiated in such embodiments, the duty cycle may be controlled based on changes in the sleep cycle, that is, the current may be provided during a period of sleep, and turned off when the patient transitions to a new phase, or according to combinations of phases.

Alternatively, the duty cycle may be controlled solely on a time basis, that is, initiated a given amount of time after the onset of sleep, and cycled at a predetermined interval thereafter until the subject awakens. Preferably, the duty cycle of the therapeutic current delivery is on greater than 5% of the time. More preferably, the duty cycle of the therapeutic current delivery is on greater than 10% of the time. Still more preferably, the duty cycle of the therapeutic current delivery is on greater than 15% of the time. Even more preferably, the duty cycle of the therapeutic current delivery is on greater than 20% of the time. Yet more preferably, the duty cycle of the therapeutic current delivery is on greater than 25% of the time. Still yet more preferably, the duty cycle of the therapeutic current delivery is on greater than 30% of the time. Even yet more preferably, the duty cycle of the therapeutic current delivery is on greater than 35% of the time. Even still more preferably, the duty cycle of the therapeutic current delivery is on greater than 40% of the time. Even still yet more preferably, the duty cycle of the therapeutic current delivery is on greater than 45% of the time.

Another way to characterize the provision of the therapeutic current to the subject is in terms of the total time of each "on" cycle. Preferably, the current is provided for at least 10 minutes continuously. More preferably, the current is provided for at least 20 minutes continuously. Still more preferably, the current is provided for at least 30 minutes continuously. Even more preferably, the current is provided for at least 40 minutes continuously. Yet more preferably, the current is provided for at least 45 minutes continuously. Still yet more preferably, the current is provided for at least 50 minutes continuously. Even still more preferably, the current is provided for at least 60 minutes continuously.

With regard to the "off" cycle, preferably the current is off for at least 10 minutes before being turned on again. More preferably, the current is off for at least 20 minutes before being turned on again. Still more preferably, the current is off for at least 30 minutes before being turned on again. Yet more preferably, the current is off for at least 45 minutes before being turned on again. Even still more preferably, the current is off for at about 60 minutes before being turned on again.

Another component of many embodiments of the present invention is a current gent generator for providing a low-dose (low current) electrical stimulation impulse through the at least one electrode for providing a low dose direct electrical current to the subject. The current generator is preferably able to provide a sustained direct current with little to no variability in amperage. By sustained, it is meant that preferably the current generator is capable of providing the current according to the varying requirements of the control program as described above. Additionally, the current generator is preferably capable of providing an alternating current at a known frequency and amplitude in order to measure electrical impedance of the electrodes as described above. Alternatively, a second current generator may be provided, thus having one generator for providing the therapeutic direct current, and a second generator for providing an alternating current for electrode impedance measurement.

Now referring to FIGS. 1-9, FIG. 1 portrays a subject 100, lying sleep, wearing one embodiment of the device 102 and 104. In this figure, the subject 100, or another person, has placed the device 102 and 104 upon his head and he is now asleep. The particular embodiment of the device depicted in this figure comprises a head band 102 enclosure that encompasses the subject's 100 head and holds the electrode array 104 securely in place contacting the subject's 100 skin. The individual electrodes are affixed to, embedded in, or otherwise integrated into a pad that is easily attached to the subject and remains securely in place through the subject's sleep time 108. The electrode array 104 in this embodiment is shown to be a 4×1 array with one central anodal electrode for delivering the therapeutic tDCS current (not shown) to the subject's brain, and four (only three visible) return electrodes to draw the current back out of the subject's brain. As described, the head band can be secured about the subject's 100 head by any means commonly known to those of skill in the art, or later developed.

Once the subject 100 dons the device 102 and 104 and falls asleep, the tDCS therapy (not shown) can be applied according to several parameters while the subject 100 is asleep 110. The system is not designed to replace medication, but rather to supplement its use. Normally, when a subject or patient goes to sleep, the medication wears off over time, and the subject or patient awakens with noticeably worse symptoms due to the low or non-existent concentration of drugs in his or her system. However, the application of a therapeutic tDCS current to the subject's brain while he or she sleeps helps to counteract the fall-off of the medication in the subject's blood stream and minimize the resulting increase in symptom occurrence and severity 112, and may even help decrease the amount of medication needed while awake 106.

Figure 2:
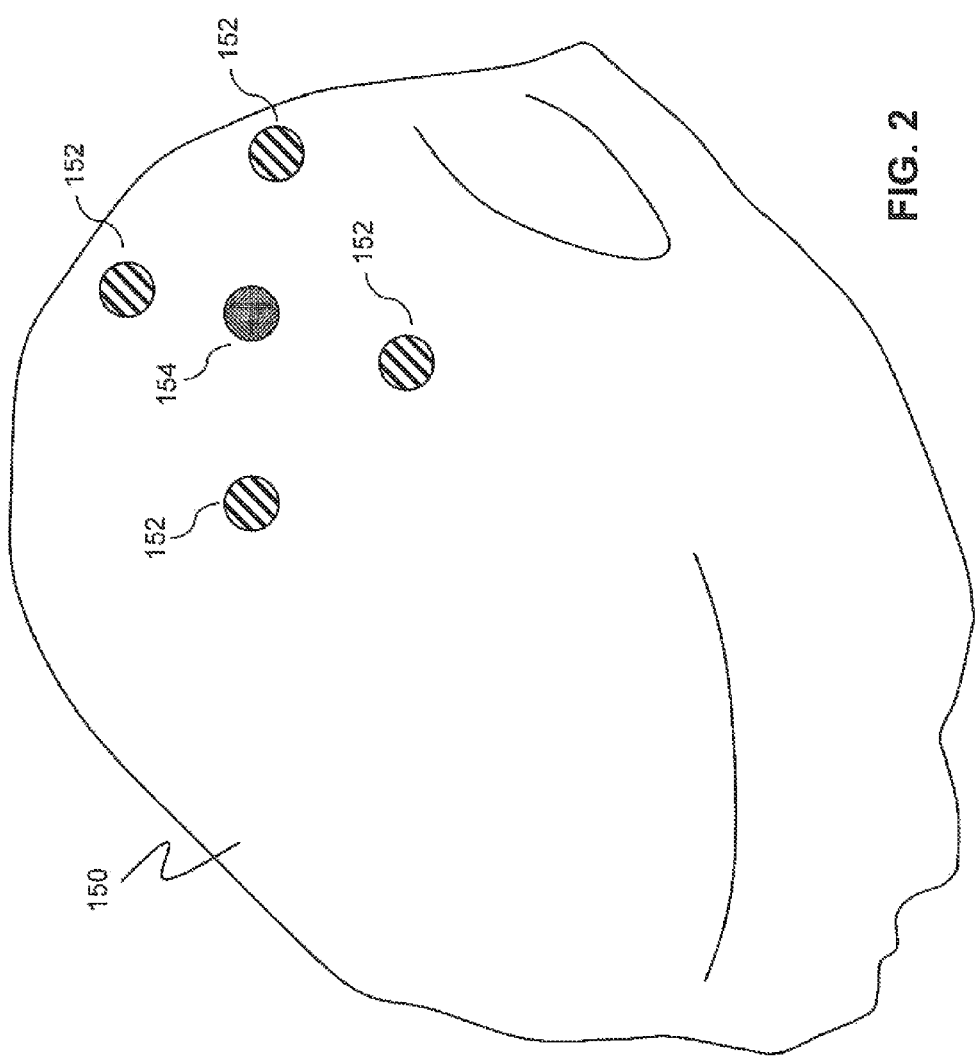
FIG. 2. is a diagram of one embodiment of the present invention comprising a custom-fitted head-worn wearable apparatus with a 4×1 electrode array affixed to or embedded into the wearable.

FIG. 2 portrays a particular embodiment of the present invention wherein the device is a custom-molded cap-style wearable apparatus 150. In such embodiments, the cap is custom molded to fit each particular subject's head. The electrodes, or electrode array, are again affixed to, embedded in, or otherwise integrated into the wearable cap 150. In this particular embodiment, the electrodes 152 and 154 are again arranged into a 4×1 electrode array comprising a central anodal electrode 154 for delivering the therapeutic tDCS current, and four return electrodes 152 for drawing the current back out. The electrodes 152 and 154 or electrode array can be fitted, attached, or integrated directly into the material of the wearable cap 150, or can be so attached to a patch which is then affixed to, embedded in, or otherwise attached to the wearable cap. In all embodiments, the electrodes 152 and 154 or the electrode array are preferably easily removed, individually, to be replaced. An individual electrode may be replaced, or the entire array may be replaced, as necessary, but no matter the arrangement, removal and insertion of new electrodes is easy and requires no formal training. Furthermore, the custom-fitted cap 150 provides the best model for repeated, sustainable placement of the electrodes in the desired location, with minimum opportunity for incorrect donning and improper placement of the electrodes. Each time the subject dons the cap 150, the electrodes will be located in the exact same desired location.

Figure 3:
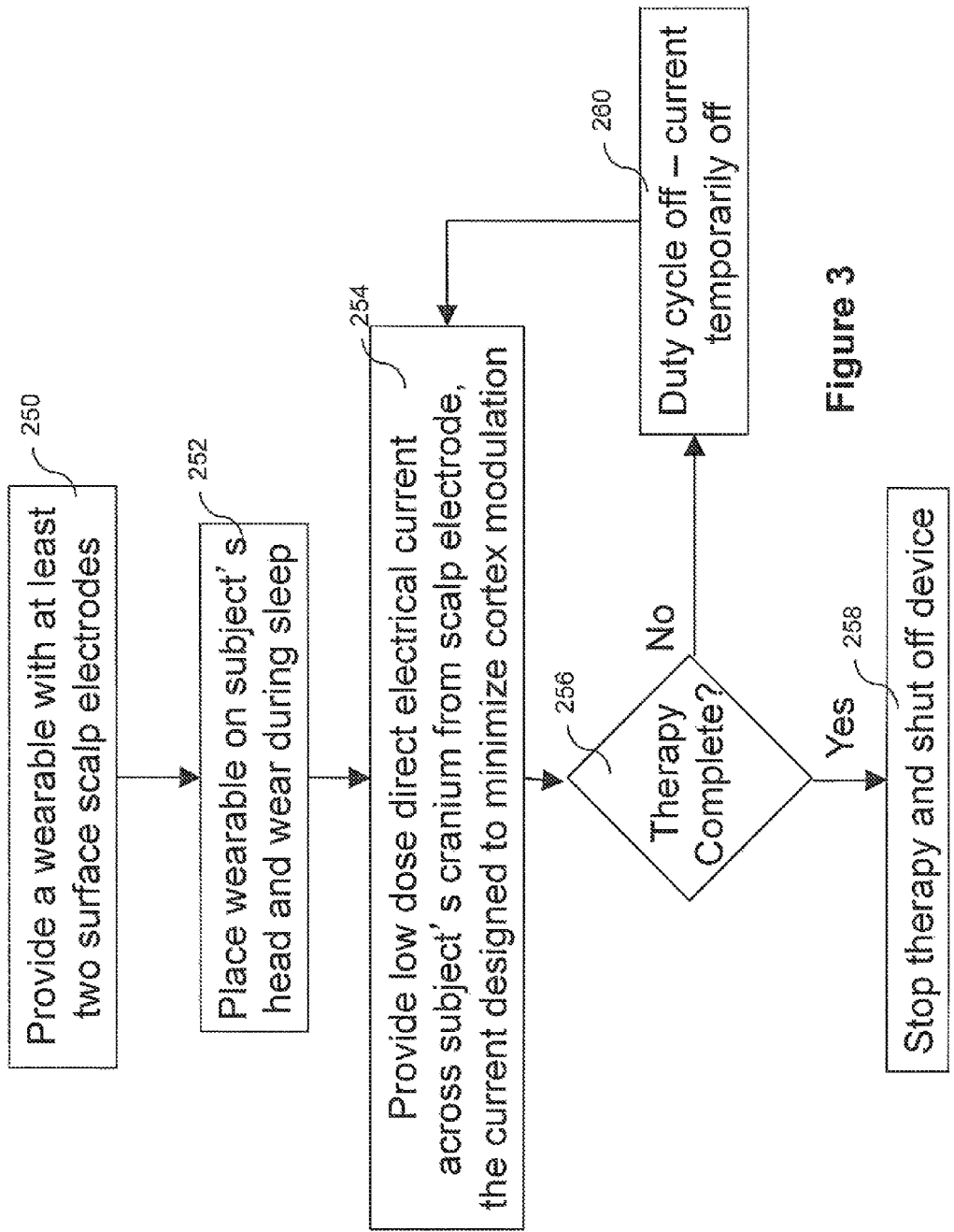
FIG. 3. is a flow chart depicting one embodiment of a method of the present invention whereby cortical modulation is minimized during tDCS therapy.

FIG. 3 depicts a flow chart of one embodiment of a method of the present invention. First, a wearable comprising at least two surface scalp electrodes is provided 250. The wearable can be of any variety described above, including, but not limited to, a custom fit cap, a belt or band, an adjustable cap, or any other variety of wearable which can be worn comfortably yet securely and in a stable manner about the subject's head. Of the at least two electrodes, one is for providing a therapeutic tDCS current across the subject's scalp and cranium and into his or her brain, and the at least one other electrode is used to draw the current back out of the subject. The electrodes are preferably dry surface scalp electrodes which require little or no preparation of the skin, little or no electrolytic or other conductive fluids or gels, and no implantation into the subject. The electrodes are merely affixed to, embedded in, or otherwise attached to the wearable.

Next, the wearable comprising the at least two electrodes is placed on the subject's head to be worn while the subject is asleep 252. The method of donning the wearable depends on the particular form the wearable takes. Regardless of said form, the wearable apparatus is placed on the subject's head, and he or she then settles in to go to sleep. Once the subject is asleep, a low dose electrical current is applied from one of the at least two electrodes, across the subject's scalp and cranium 254. The current is applied according to a predetermined duty cycle as described above, and the electrodes are placed in such a manner as to apply the current to target a particular portion of the subject's brain that corresponds to at least one symptom of a movement disorder. Applying the tDCS current in this manner thus reduces the occurrence, severity, and or duration of movement disorder symptom activity for the subject. In the particular embodiment depicted in this figure, the tDCS current is applied in a manner so as to minimize cortex modulation in the frontal region, contralateral region, and occipital lobe of the subject's brain. The tDCS therapy continues according to the predetermined duty cycle until the patient awakes. If the system detects that the therapy session is complete (e.g. patient awakens, predetermined time period of therapy has lapsed, predetermined number of therapeutic cycles have completed, sleep stage as changed, etc.) 256, the therapy session stops 258, and no further current is applied. However, if the therapy session is not complete (i.e., the patient is still asleep, predetermined number of therapeutic cycles has not completed, sleep stage indicates therapy should continue, etc.) the therapy continues, that is the duty cycle off period begins (the current is temporarily turned off) 260, until the system detects or determines that the duty cycle on period should begin again, and the current is turned on 254. This process is then repeated until the therapy session is completed.

Figure 4:
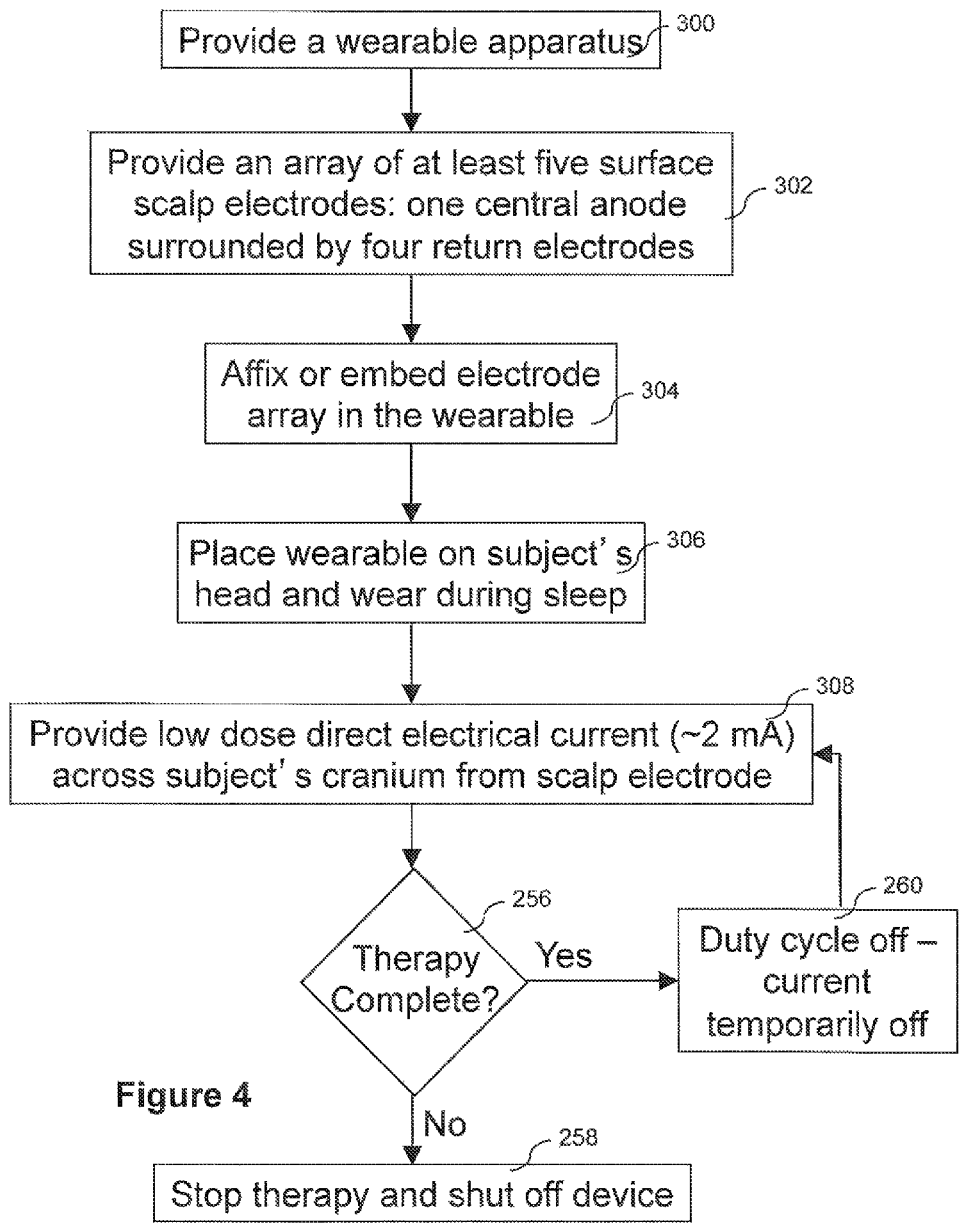
FIG. 4. is a flow chart depicting another embodiment of a method of the present invention whereby at least 5 electrodes are provided in an array and tDCS therapy is provided with an electrical current of 2 milli-amps (mA).

FIG. 4 is a flow chart of another embodiment of a method of the present invention. First, a wearable apparatus is provided 300. The wearable can be of any variety described above, including, but not limited to, a custom fit cap, a belt or band, an adjustable cap, or any other variety of wearable which can be worn comfortably yet securely and in a stable manner about the subject's head. Further, an array of at least five electrodes is provided 302. The electrodes are preferably dry surface scalp electrodes which require little or no preparation of the skin, little or no electrolytic or other conductive fluids or gels, and no implantation into the subject. Preferably, the at least five electrodes are arranged in at least a 4×1 ring. There should be a single, central anodal electrode that is used to provide the therapeutic tDCS current to the subject's brain. The at least four, and any additional other electrodes, should be arranged around the central, anodal electrode in a ring structure. These outer electrodes are then utilized to draw the tDCS current back out of the subject. The electrodes are then affixed to, embedded in, or otherwise attached to the wearable as previously described 304.

Next, the wearable comprising the array of at least five electrodes is placed on the subject's head to be worn while the subject is asleep 306. The method of donning the wearable depends on the particular form the wearable takes. Regardless of said form, the wearable apparatus is placed on the subject's head, and he or she then settles in to go to sleep. Once the subject is asleep, a low dose electrical current is applied from one of the at least two electrodes, across the subject's scalp and cranium 308. In this particular embodiment, therapy is provided in constant current mode, with the low dose electrical current being provided at about 2 mA. The current is applied according to a predetermined duty cycle as described above, and the electrodes are placed in such a manner as to apply the current to target a particular portion of the subject's brain that corresponds to at least one symptom of a movement disorder. Applying the tDCS current in this manner thus reduces the occurrence, severity, and or duration of movement disorder symptom activity for the subject. Additionally, another embodiment of a similar method further includes a predetermined duty cycle of 33% (not shown), wherein the tDCS current is on for about 33% of each cycle and off for about 66% of each cycle. In such alternative embodiment, an exemplary cycle period would be 3 hours, where the tDCS current is on for one hour, off for two hours, and then repeated. In either embodiment (comprising the specific 33% duty cycle or some other duty cycle), the tDCS therapy continues according to the predetermined duty cycle until the system determines that the therapy session is complete. If the system detects that the therapy session is complete (e.g. patient awakens, predetermined time period of therapy has lapsed, predetermined number of therapeutic cycles have completed, etc.) 256, the therapy session stops 258, and no further current is applied. However, if the therapy session is not complete (i.e., the patient is still asleep, predetermined number of therapeutic cycles has not completed, sleep stage indicates therapy should continue, etc.) the therapy continues, that is the duty cycle off period begins (the current is temporarily turned off) 260, until the system detects or determines that the duty cycle on period should begin again, and the current is turned on 308. This process is then repeated until the therapy session is completed.

Figure 5:
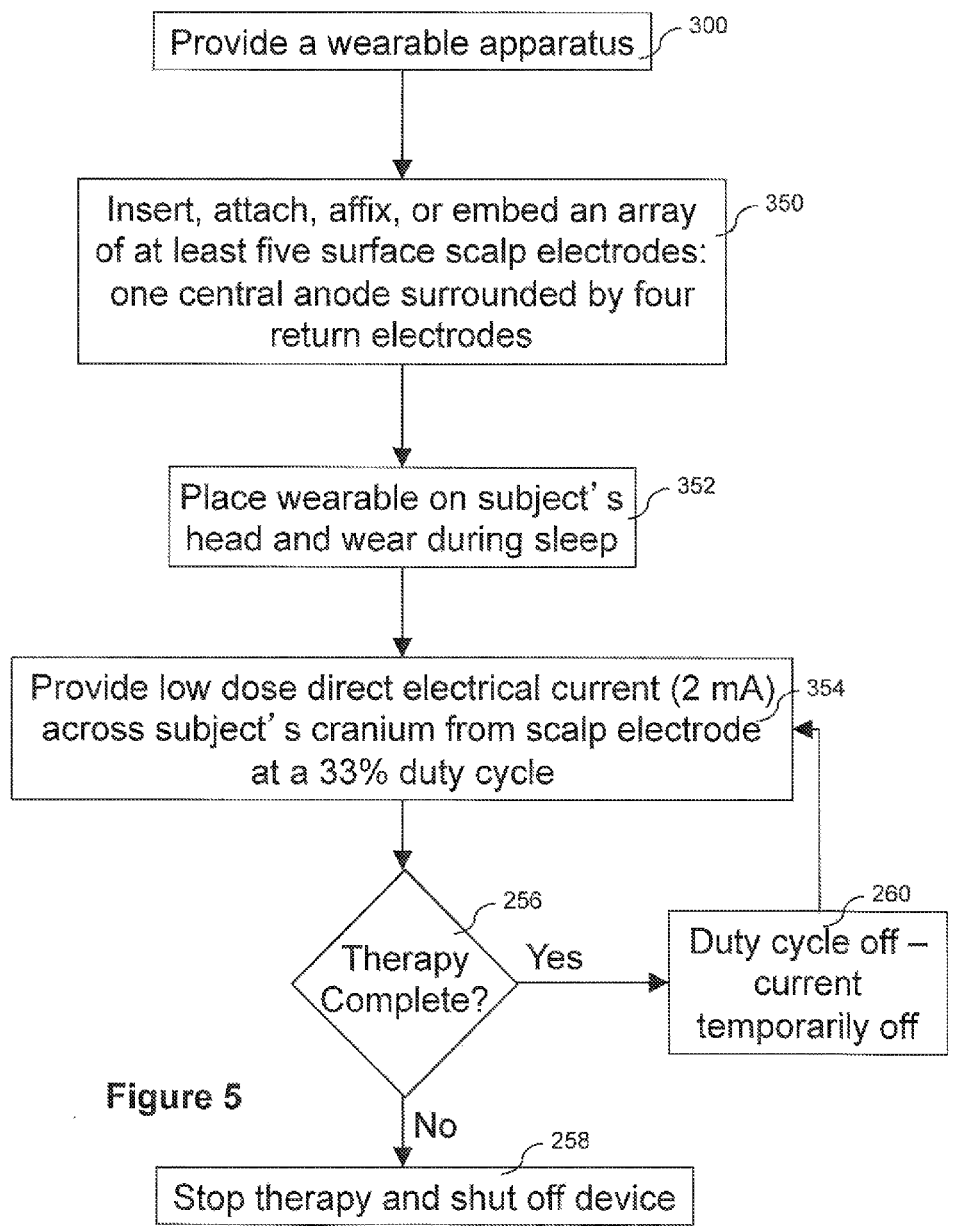
FIG. 5. is a flow chart of another embodiment of a method of the present invention including the step of attaching an array of at least 5 electrodes to a wearable apparatus to place on the subject's head, and then providing a therapeutic tDCS current of 2 mA.

FIG. 5 is a flow chart of another embodiment of a method of the present invention. First, a wearable apparatus is provided 300. The wearable can be of any variety described above, including, but not limited to, a custom fit cap, a belt or band, an adjustable cap, or any other variety of wearable which can be worn comfortably yet securely and in a stable manner about the subject's head. Next, an array of at least 5 surface scalp electrodes is affixed to, embedded in, or otherwise attached to the wearable as previously described 350. The electrodes are preferably dry surface scalp electrodes which require little or no preparation of the skin, little or no electrolytic or other conductive fluids or gels, and no implantation into the subject. Preferably, the at least five electrodes are arranged in at least a 4×1 ring. There should be a single, central anodal electrode that is used to provide the therapeutic tDCS current to the subject's brain. The at least four, and any additional other electrodes, should be arranged around the central, anodal electrode in a ring structure. These outer electrodes are then utilized to draw the tDCS current back out of the subject.

Next, the wearable comprising the array of at least five electrodes is placed on the subject's head to be worn while the subject is asleep 352. The method of donning the wearable depends on the particular form the wearable takes. Regardless of said form, the wearable apparatus is placed on the subject's head, and he or she then set-ties in to go to sleep. Once the subject is asleep, a low dose electrical current is applied from one of the at least two electrodes, across the subject's scalp and cranium 354. The current is applied according to a predetermined duty cycle as described above, and the electrodes are placed in such a manner as to apply the current to target a particular portion of the subject's brain that corresponds to at least one symptom of a movement disorder. Applying the tDCS current in this manner thus reduces the occurrence, severity, and or duration of movement disorder symptom activity for the subject. In the particular embodiment depicted in this figure, the tDCS current is applied at substantially 2 mA (milli-amps), and the duty cycle is about 33%. The tDCS therapy continues according to the predetermined duty cycle until the patient awakes. If the system detects that the therapy session is complete (e.g. patient awakens, predetermined time period of therapy has lapsed, predetermined number of therapeutic cycles have completed, etc.) 256, the therapy session stops 258, and no further current is applied. However, if the therapy session is not complete (i.e., the patient is still asleep, predetermined number of therapeutic cycles has not completed, sleep stage indicates therapy should continue, etc.) the therapy continues, that is the duty cycle off period begins (the current is temporarily turned off) 260, until the system detects or determines that the duty cycle on period should begin again, and the current is turned on 354. This process is then repeated until the therapy session is completed.

Figure 6:
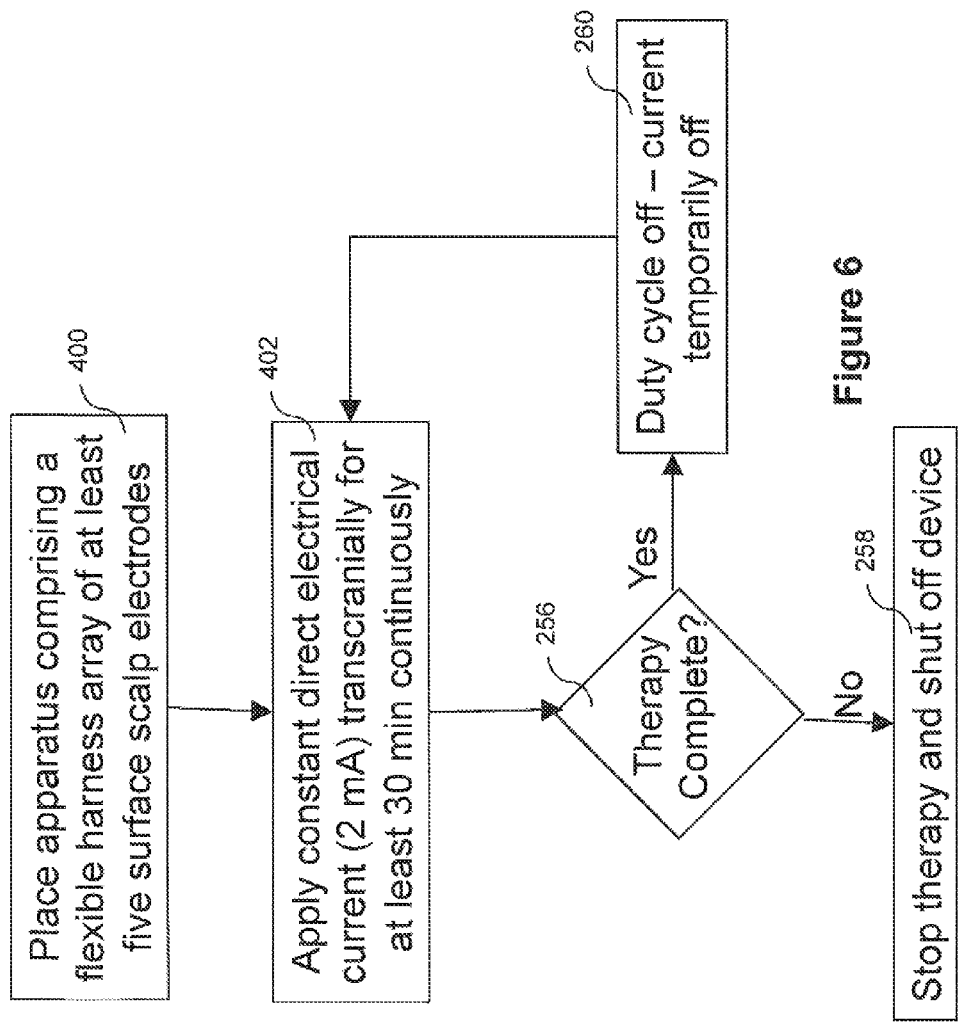
FIG. 6. is a flow chat of yet another embodiment of a method of the present invention whereby an apparatus comprising at least 5 electrodes in an array is provided and a tDCS therapeutic current is applied at 2 mA for a minimum of 30 minutes continuously.

FIG. 6 is a flow chart of another embodiment of a method of the present invention. First, a flexible apparatus and an electrode array are provided and placed upon a subject's head 400. In this particular embodiment, the wearable is some variety of a flexible harness. Further, in this particular embodiment, the electrode array is not affixed to or embedded into the harness, but rather the array and the harness are separate, individual pieces, and the flexible harness is used to hold the array in place once placed on the subject's head. As above, the harness may be secured above the subject's head in any manner commonly known to those of skill in the art. Further, the electrodes of the electrode array are preferably dry surface scalp electrodes which require little or no preparation of the skin, little or no electrolytic or other conductive fluids or gels, and no implantation into the subject. Preferably, the at least five electrodes are arranged in at least a 4×1 ring. There should be a single, central anodal electrode that is used to provide the therapeutic tDCS current to the subject's brain. The at least four, and any additional other electrodes, should be arranged around the central, anodal electrode in a ring structure. These outer electrodes are then utilized to draw the tDCS current back out of the subject. The array may, and preferably, is additionally secured to the subject's head by means of an adhesive layer which adheres the array to the subject's scalp. The flexible harness then provides additional stability and security to the placement of the electrode array.

Once the array and harness are placed onto the subject's head, a low dose electrical current is applied from one of the at least two electrodes, across the subject's scalp and cranium 402. The current is applied according to a predetermined duty cycle as described above, and the electrodes are placed in such a manner as to apply the current to target a particular portion of the subject's brain that corresponds to at least one symptom of a movement disorder. In this particular embodiment, the tDCS current is applied substantially at 2 mA and the on-time for the current is at least 30 minutes. Thus, for example, if the duty cycle is 33%, where the current is on for thirty minutes, the 33% duty cycle then dictates that the current would be off for one hour before reinitiating the on-cycle. However, the current may be on for longer than 30 minutes, and the duty cycle may be other than 33%, or may be dynamically adjusted based on the subject's needs substantially in real time, in which case the off-period would adjust accordingly to maintain the appropriate duty cycle. The tDCS therapy continues according to the duty cycle until the patient awakes. If the system detects that the therapy session is complete (e.g. patient awakens, predetermined time period of therapy has lapsed, predetermined number of therapeutic cycles have completed, etc.) 256, the therapy session stops 258, and no further current is applied. However, if the therapy session is not complete (i.e., the patient is still asleep, predetermined number of therapeutic cycles has not completed, sleep stage indicates therapy should continue, etc.) the therapy continues, that is the duty cycle off period begins (the current is temporarily turned off) 260, until the system detects or determines that the duty cycle on period should begin again, and the current is turned on 402. This process is then repeated until the therapy session is completed.

Figure 7:
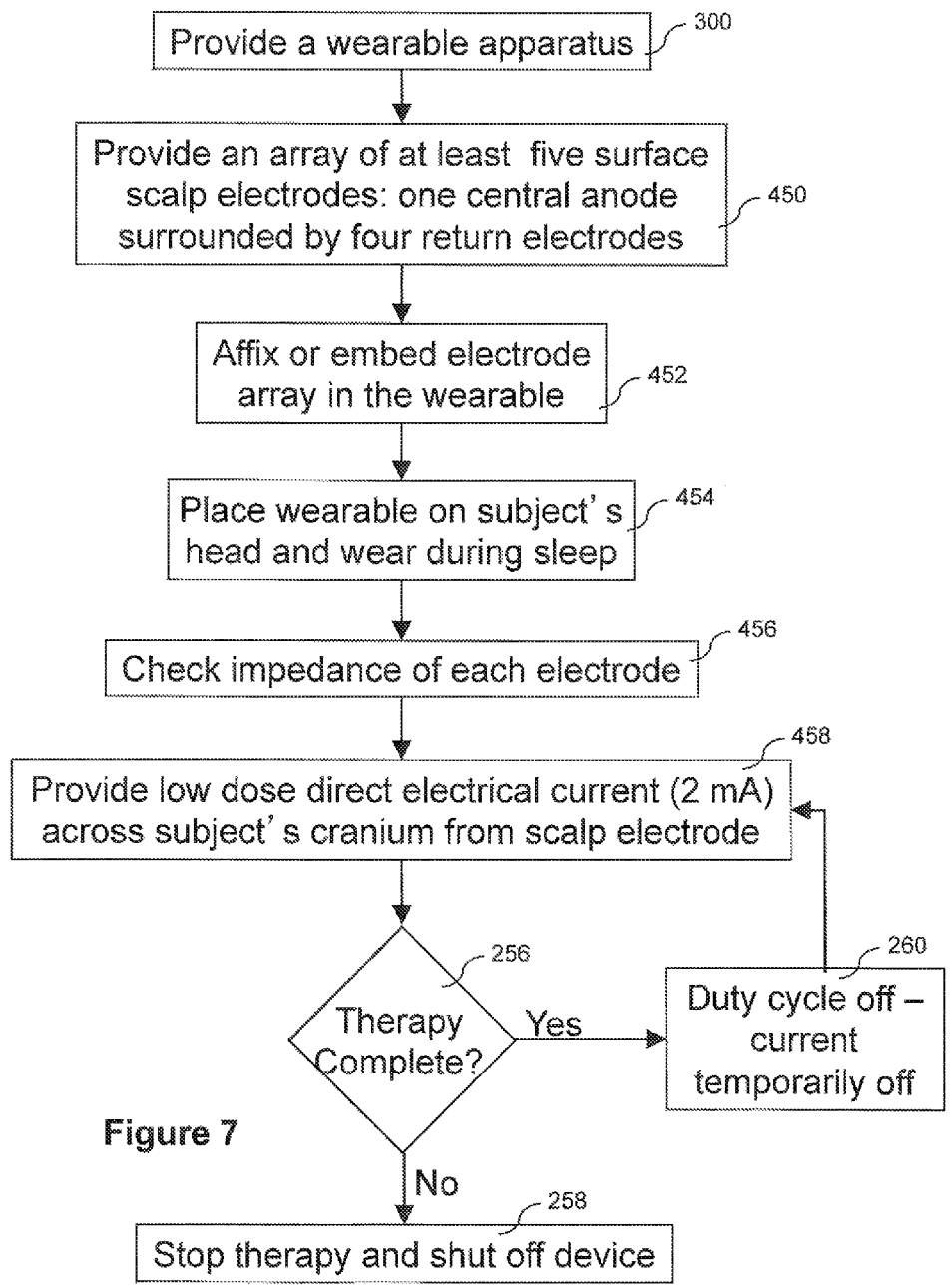
FIG. 7. is a flow chart of still another embodiment of a method of the present invention whereby an array of at least 5 electrodes is provided and the electrical impedance of each the at least two electrodes is checked in order to ensure a strong, proper connection between the electrodes and the subject's scalp.

FIG. 7 is a flow chart of another embodiment of a method of the present invention. First, a wearable apparatus is provided 300. The wearable can be of any variety described above, including, but not limited to, a custom fit cap, a belt or band, an adjustable cap, or any other variety of wearable which can be worn comfortably yet securely and in a stable manner about the subject's head. Further, an array of at least five electrodes is provided 450. The electrodes are preferably dry surface scalp electrodes which require little or no preparation of the skin, little or no electrolytic or other conductive fluids or gels, and no implantation into the subject. Preferably, the at least five electrodes are arranged in at least a 4×1 ring. There should be a single, central anodal electrode that is used to provide the therapeutic tDCS current to the subject's brain. The at least four, and any additional other electrodes, should be arranged around the central, anodal electrode in a ring structure. These outer electrodes are then utilized to draw the tDCS current back out of the subject. The electrodes are then affixed to, embedded in, or otherwise attached to the wearable as previously described 452.

Next, the wearable comprising the array of at least five electrodes is placed on the subject's head to be worn while the subject is asleep 454. The method of donning the wearable depends on the particular form the wearable takes. Regardless of said form, the wearable apparatus is placed on the subject's head, and he or she then settles in to go to sleep. Once the wearable is placed on the subject's head (regardless of whether subject is asleep), the system may then check the electrical impedance of each of the electrodes 456. The impedance check can be performed according to any of the methods disclosed above. However, before the therapeutic tDCS current is applied, the electrical impedance of each electrode must be checked and verified to be low enough in order for the therapy cycle to begin. In the event that an electrode's impedance is too high, the system will notify the subject or user to replace that electrode. Only then will the therapy session be able to begin.

Once the electrodes are all verified to be in proper working condition, the current is applied according to a predetermined duty cycle as described above, and the electrodes are placed in such a manner as to apply the current to target a particular portion of the subject's brain that corresponds to at least one symptom of a movement disorder 458. Applying the tDCS current in this manner thus reduces the occurrence, severity, and or duration of movement disorder symptom activity for the subject. In the particular embodiment depicted in this figure, the tDCS current is applied at substantially 2 mA (milli-amps). The tDCS therapy continues according to the predetermined duty cycle until the patient awakes. If the system detects that the therapy session is complete (e.g. patient awakens, predetermined time period of therapy has lapsed, predetermined number of therapeutic cycles have completed, etc.) 256, the therapy session stops 258, and no further current is applied. However, if the therapy session is not complete (i.e., the patient is still asleep, predetermined number of therapeutic cycles has not completed, sleep stage indicates therapy should continue, etc.) the therapy continues, that is the duty cycle off period begins (the current is temporarily turned off) 260, until the system detects or determines that the duty cycle on period should begin again, and the current is turned on 458. This process is then repeated until the therapy session is completed.

Figure 8:
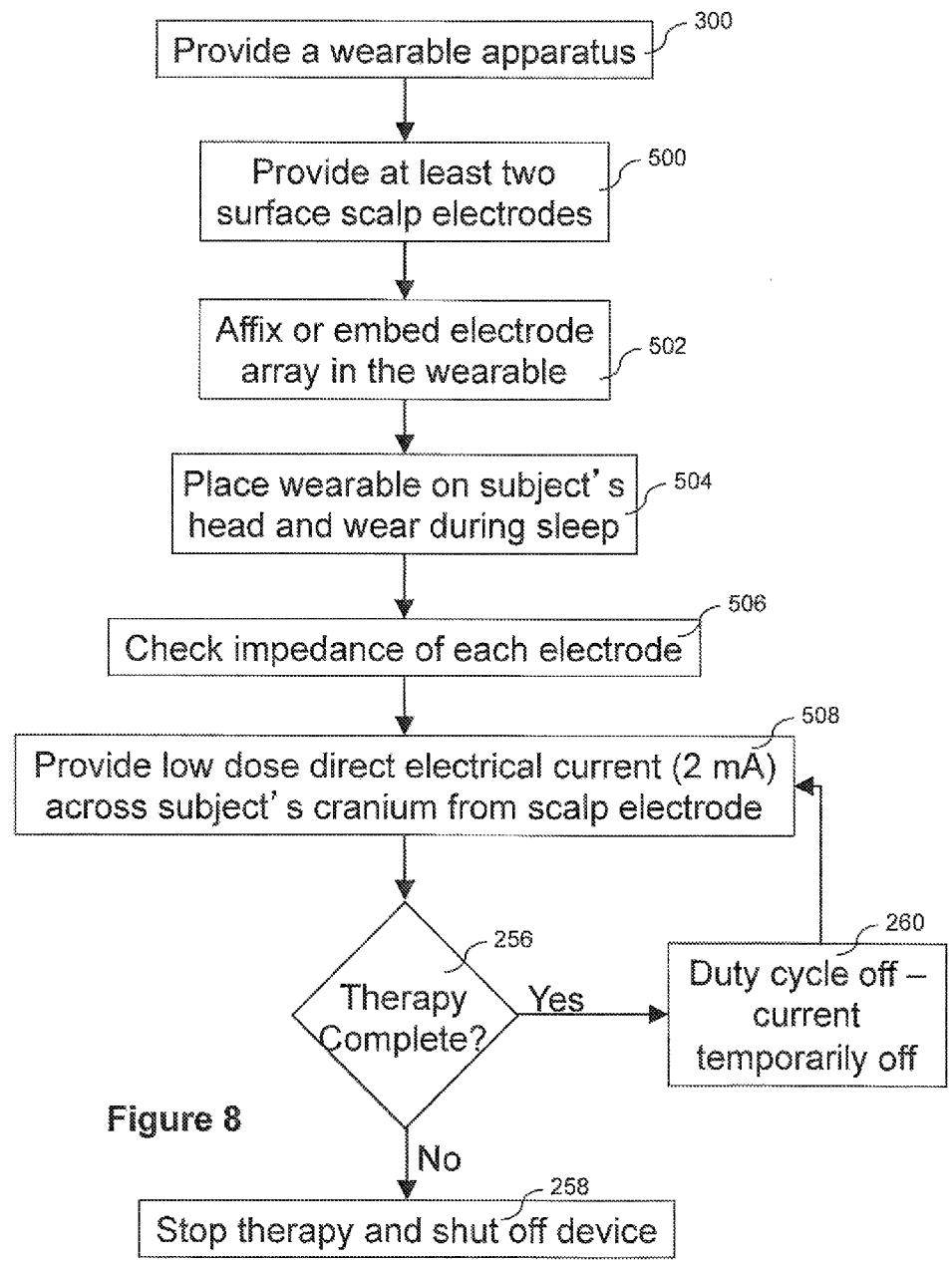
FIG. 8. is a flow chart of still yet another embodiment of a method of the present invention whereby at least two electrodes are provided and the electrical impedance of the at least 2 electrode array is checked in order to ensure a strong, proper connection between the electrodes and the subject's scalp.

FIG. 8 is a flow chart of another embodiment of a method of the present invention. First, a wearable apparatus is provided 300. The wearable can be of any variety described above, including, but not limited to, a custom fit cap, a belt or band, an adjustable cap, or any other variety of wearable which can be worn comfortably yet securely and in a stable manner about the subject's head. Further, at least two electrodes are provided 500, one of which is for providing a therapeutic tDCS current across the subject's scalp and cranium and into his or her brain, and the at least one other electrode is used to draw the current back out of the subject. The electrodes are preferably dry surface scalp electrodes which require little or no preparation of the skin, little or no electrolytic or other conductive fluids or gels, and no implantation into the subject. The electrodes are then affixed to, embedded in, or otherwise attached to the wearable as previously described 502.

Next, the wearable comprising the at least two electrodes is placed on the subject's head to be worn while the subject is asleep 504. The method of donning the wearable depends on the particular form the wearable takes. Regardless of said form, the wearable apparatus is placed on the subject's head, and he or she then settles in to go to sleep. Once the wearable is placed on the subject's head (regardless of whether subject is asleep), the system may then check the electrical impedance of each of the electrodes 506. The impedance check can be performed according to any of the methods disclosed above. However, before the therapeutic tDCS current is applied, the electrical impedance of each electrode must be checked and verified to be low enough in order for the therapy cycle to begin. In the event that an electrode's impedance is too high, the system will notify the subject or user to replace that electrode. Only then will the therapy session be able to begin.

Once the electrodes are all verified to be in proper working condition, the current is applied according to a predetermined duty cycle as described above, and the electrodes are placed in such a manner as to apply the current to target a particular portion of the subject's brain that corresponds to at least one symptom of a movement disorder 508. Applying the tDCS current in this manner thus reduces the occurrence, severity, and or duration of movement disorder symptom activity for the subject. In the particular embodiment depicted in this figure, the tDCS current is applied at substantially 2 mA (milli-amps). The tDCS therapy continues according to the predetermined duty cycle until the patient awakes. If the system detects that the therapy session is complete (e.g. patient awakens, predetermined time period of therapy has lapsed, predetermined number of therapeutic cycles have completed, etc.) 256, the therapy session stops 258, and no further current is applied. However, if the therapy session is not complete (i.e., the patient is still asleep, predetermined number of therapeutic cycles has not completed, sleep stage indicates therapy should continue, etc.) the therapy continues, that is the duty cycle off period begins (the current is temporarily turned off) 260, until the system detects or determines that the duty cycle on period should begin again, and the current is turned on 508. This process is then repeated until the therapy session is completed.

Figure 9:
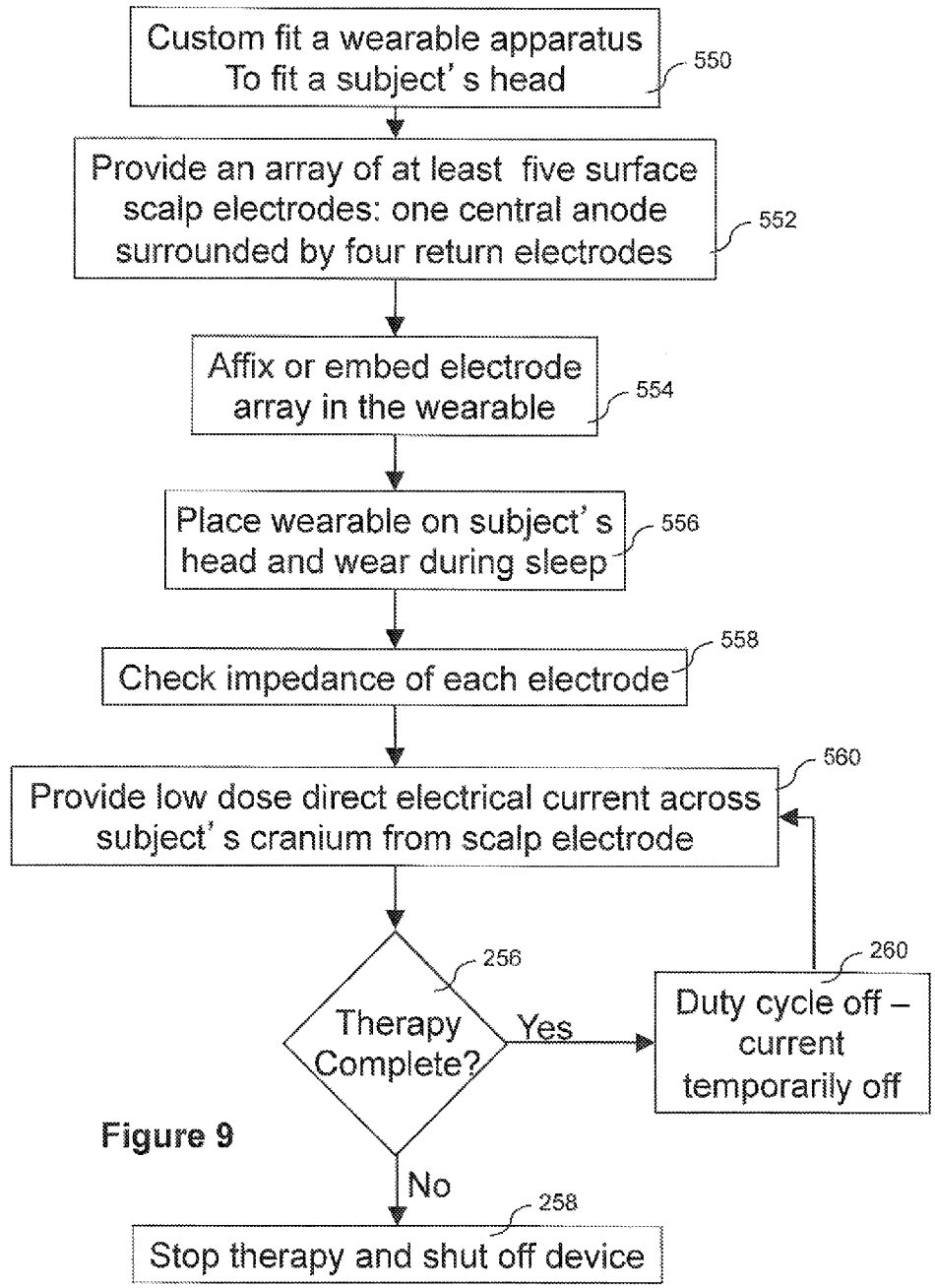
FIG. 9. is a flow chart of still another embodiment of a method of the present invention whereby wearable is custom-fitted to a particular subject's head, an array of at least 5 electrodes is provided and the electrical impedance of each the at least two electrodes is checked in order to ensure a strong, proper connection between the electrodes and the subject's scalp.

FIG. 9 is a flow chart of another embodiment of a method of the present invention. First, a wearable apparatus is custom fitted to fit a subject's head 500. The wearable can be made of any material and/or method commonly known to those in the art, and should be able to be worn comfortably yet securely and in a stable manner about the subject's head. In order to custom fit the wearable to a particular subject, the subject will likely need to be present for a consultation in which measurements are taken, a mold is made, or some other precise modeling method is used. The modeling method may be any of those currently known to those of skill in the art, or any method later developed. The measurement, mold, or model can then be used to create a custom-fit wearable that conforms to the particular shape, size, and contours of the subject's head. This method further helps to provide precise, repeatable placement of the electrodes each time the subject dons the wearable.

Further, an array of at least five electrodes is provided 552. The electrodes are preferably dry surface scalp electrodes which require little or no preparation of the skin, little or no electrolytic or other conductive fluids or gels, and no implantation into the subject. Preferably, the at least five electrodes are arranged in at least a 4×1 ring. There should be a single, central anodal electrode that is used to provide the therapeutic tDCS current to the subject's brain. The at least four, and any additional other electrodes, should be arranged around the central, anodal electrode in a ring structure. These outer electrodes are then utilized to draw the tDCS current back out of the subject. The electrodes are then affixed to, embedded in, or otherwise attached to the wearable as previously described 554.

Next, the wearable comprising the array of at least five electrodes is placed on the subject's head to be worn while the subject is asleep 556. The method of donning the wearable depends on the particular form the wearable takes. Regardless of said form, the wearable apparatus is placed on the subject's head, and he or she then settles in to go to sleep. Once the wearable is placed on the subject's head (regardless of whether subject is asleep), the system may then check the electrical impedance of each of the electrodes 558. The impedance check can be performed according to any of the methods disclosed above. However, before the therapeutic tDCS current is applied, the electrical impedance of each electrode must be checked and verified to be low enough in order for the therapy cycle to begin. In the event that an electrode's impedance is too high, the system will notify the subject or user to replace that electrode. Only then will the therapy session be able to begin.

Once the electrodes are all verified to be in proper working condition, the current is applied according to a predetermined duty cycle as described above, and the electrodes are placed in such a manner as to apply the current to target a particular portion of the subject's brain that corresponds to at least one symptom of a movement disorder 560. Applying the tDCS current in this manner thus reduces the occurrence, severity, and or duration of movement disorder symptom activity for the subject. The tDCS therapy continues according to the predetermined duty cycle until the patient awakes. If the system detects that the therapy session is complete (e.g. patient awakens, predetermined time period of therapy has lapsed, predetermined number of therapeutic cycles have completed, etc.) 256, the therapy session stops 258, and no further current is applied. However, if the therapy session is not complete (i.e., the patient is still asleep, predetermined number of therapeutic cycles has not completed, sleep stage indicates therapy should continue, etc.) the therapy continues, that is the duty cycle off period begins (the current is temporarily turned off) 260, until the system detects or determines that the duty cycle on period should begin again, and the current is turned on 560. This process is then repeated until the therapy session is completed.

Figure 10:
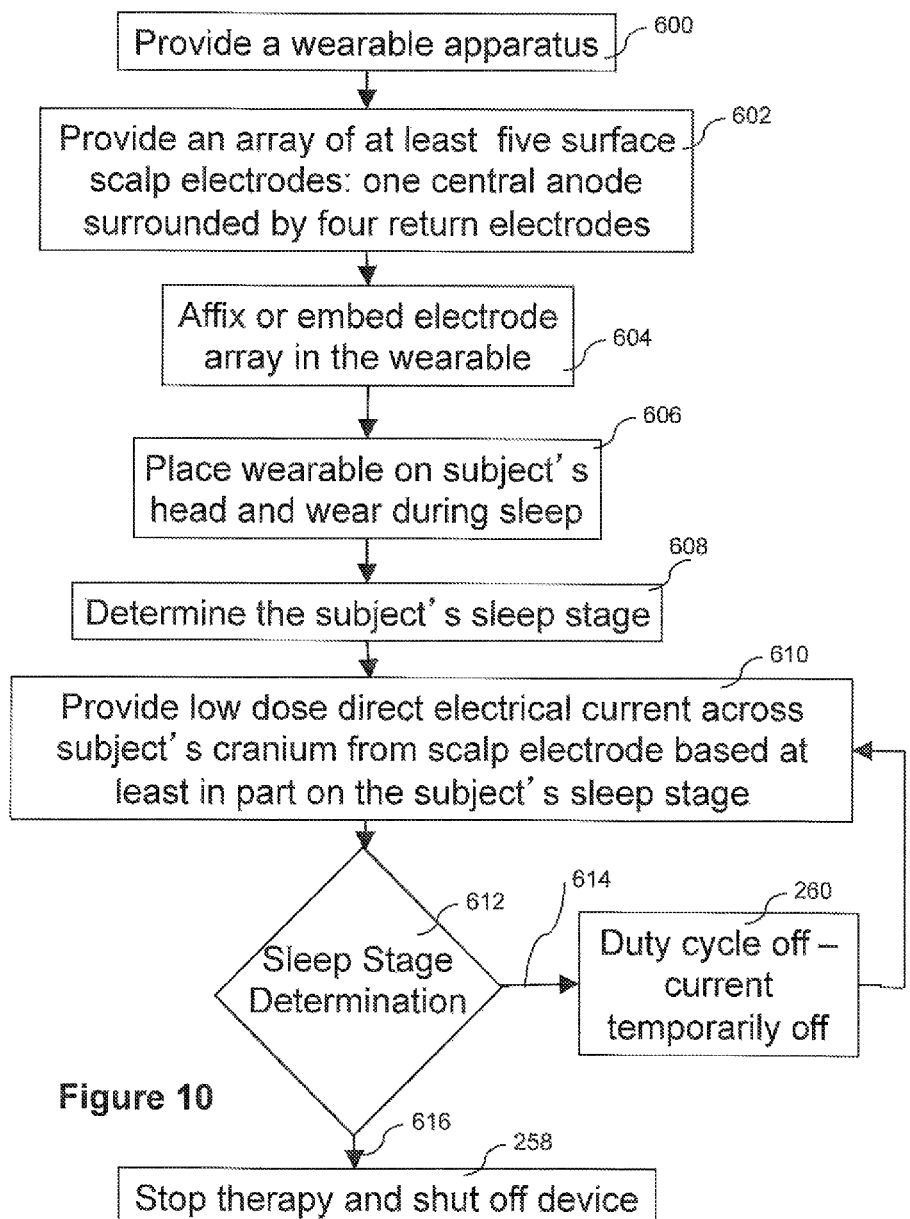
FIG. 10. is a flow chart of another embodiment of a method of the present invention including the step of attaching an array of at least 5 electrodes to a wearable apparatus to place on the subject's head, determining the stage of sleep the subject is in, and then starting to provide a therapeutic tDCS current based on the determined sleep stage.

FIG. 10 is a flow chart of another embodiment of a method of the present invention. First, a wearable apparatus is provided 600. The wearable can be of any variety described above, including, but not limited to, a custom fit cap, a belt or band, an adjustable cap, or any other variety of wearable which can be worn comfortably yet securely and in a stable manner about the subject's head. Further, an array of at least five electrodes is provided 602. The electrodes are preferably dry surface scalp electrodes which require little or no preparation of the skin, little or no electrolytic or other conductive fluids or gels, and no implantation into the subject. Preferably, the at least five electrodes are arranged in at least a 4×1 ring. There should be a single, central anodal electrode that is used to provide the therapeutic tDCS current to the subject's brain. The at least four, and any additional other electrodes, should be arranged around the central, anodal electrode in a ring structure. These outer electrodes are then utilized to draw the tDCS current back out of the subject. The electrodes are then affixed to, embedded in, or otherwise attached to the wearable as previously described 604.

Next, the wearable comprising the array of at least five electrodes is placed on the subject's head to be worn while the subject is asleep 606. The method of donning the wearable depends on the particular form the wearable takes. Regardless of said form, the wearable apparatus is placed on the subject's head, and he or she then settles in to go to sleep. Once the apparatus with electrode array is placed on the subject's head and the subject falls asleep, the system then begins to monitor the subject's sleep stage 608. The system may use any means currently known to those in the art, or later developed, in order to determine the sleep stage in which the subject is sleeping. By way of non-limiting example, an EEG signal may be used to determine the subject's sleep stage. This sleep stage determination is preferably made substantially in real-time, and the system then turns on the therapeutic, thus beginning the duty cycle, of the tDCS therapy. The particular sleep stage which triggers the beginning of the therapy cycle may be different for individual subjects, symptoms being treated, or any other variable. The therapeutic current is applied according to a predetermined duty cycle, and based at least in part on the detected sleep stage of the subject, as described above, and the electrodes are placed in such a manner as to apply the current to target a particular portion of the subject's brain that corresponds to at least one symptom of a movement disorder 610. Further, the stimulation applied may be changed throughout a given therapy session based on factors such as sleep stage, or the like. Applying the tDCS current in this manner thus reduces the occurrence, severity, and/or duration of movement disorder symptom activity for the subject. The tDCS therapy continues according to the predetermined duty cycle until the patient awakes. If the system detects that the therapy session is complete because the subject has entered a different sleep stage that does not correspond to the desired treatment, or the therapy session otherwise is determined to be complete (e.g. patient awakens, predetermined time period of therapy has lapsed, predetermined number of therapeutic cycles have completed, etc.) 612, the therapy session stops 258, and no further current is applied. In the depicted embodiment, the main determinant is the subject's sleep stage. If, for example, the therapy is predetermined to only occur (i.e., tDCS current supplied) while the subject is in REM sleep, then when the system determines that the subject leaves REM sleep, the system determines 616 to shut off the current and stop therapy 258. Conversely, if the system determines that the subject is still in the desired stage of sleep but the duty cycle or predetermined time period for current on-time has completed, the system determines 614 that the current should be temporarily shut off, and that the duty cycle should control 260 when the therapeutic current is again turned on 610. This process is then repeated until the therapy session is completed.

While a preferred embodiment is disclosed herein, it will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A method of providing therapy for movement disorder symptoms comprising steps of:
  providing a wearable apparatus comprising at least two surface scalp electrodes, at least one electrode for providing a low dose direct electrical current to the patient, and at least one electrode for return of the low dose direct electrical current;
  placing the apparatus on a subject's head and having the subject wear the apparatus during sleep; and
  providing a low dose direct electrical current from the at least one surface scalp electrode for providing a low dose direct electrical current across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms.

2. The method of claim 1, wherein the at least 2 electrodes are embedded in a single pad, which can be inserted or removed from the wearable as a single unit.

3. The method of claim 2, wherein the pad and electrodes are low-cost and disposable.

4. The method of claim 1, wherein the current is applied to the primary motor cortex.

5. The method of claim 1, wherein the subject experiences at least a 15% improvement in symptom occurrence, severity or duration.

6. The method of claim 1, wherein the current is applied according to at least a 33% duty cycle.

7. The method of claim 1, wherein the current is applied to stimulate production of dopamine production in the subject's brain.

8. A method of providing therapy for movement disorder symptoms comprising steps of:
  providing a wearable apparatus, providing a wearable apparatus comprising at least two surface scalp electrodes, at least one electrode for providing a low dose direct electrical current to the patient, and at least one electrode for return of the low dose direct electrical current;
  placing the apparatus on a subject's head and having the subject wear the apparatus during sleep;
  determining the subject's sleep stage substantially in real time; and
  providing a low dose direct electrical current from the at least one anodal electrode across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement and/or sleep disorder symptoms;
wherein the duty cycle for providing the low dose direct electrical current is turned on based at least in part on the determined sleep stage.

9. The method of claim 8, wherein the at least 2 electrodes are embedded in a single pad, which can be inserted or removed from the wearable as a single unit.

10. The method of claim 9, wherein the pad and electrodes are low-cost and disposable.

11. The method of claim 8, wherein the current is applied to the primary motor cortex.

12. The method of claim 8, wherein the subject experiences at least a 15% improvement in symptom occurrence, severity or duration.

13. The method of claim 8, wherein the current is applied according to at least a 33% duty cycle.

14. The method of claim 8, wherein the current is applied to stimulate production of dopamine production in the subject's brain.

15. A method of providing therapy for movement disorder symptoms comprising steps of:
providing a wearable apparatus comprising at least two surface scalp electrodes, at least one electrode for providing a low dose direct electrical current to the patient, and at least one electrode for return of the low dose direct electrical current;
placing the apparatus on a subject's head and having the subject wear the apparatus during sleep, and
providing a low dose direct electrical current from the at least one surface scalp electrode for providing a low dose direct electrical current across the subject's cranium to stimulate at least one area of the subject's brain at a pre-determined duty-cycle, the area of the subject's brain being stimulated corresponding to at least one symptom of a movement disorder to reduce the occurrence, severity, and/or duration of movement disorder symptoms;
wherein cortex modulation in frontal regions, contralateral motor regions, and occipital lobe of the subject's brain is minimized to be less than 0.01 V/m.

16. The method of claim 15, wherein the at least 2 electrodes are embedded in a single pad, which can be inserted or removed from the wearable as a single unit.

17. The method of claim 16, wherein the pad and electrodes are low-cost and disposable.

18. The method of claim 15, wherein the current is applied to the primary motor cortex.

19. The method of claim 15, wherein the subject experiences at least a 15% improvement in symptom occurrence, severity or duration.

20. The method of claim 15, wherein the current is applied according to at least a 33% duty cycle.

* * * * *